US011381659B2

(12) United States Patent
Devam et al.

(10) Patent No.: US 11,381,659 B2
(45) Date of Patent: Jul. 5, 2022

(54) REALITY-AUGMENTED MORPHOLOGICAL PROCEDURE

(71) Applicant: ARIS MD, Inc., Wilmington, DE (US)

(72) Inventors: Chandra Devam, Edmonton (CA);
Zaki Adnan Taher, Edmonton (CA);
William Scott Edgar, Sherwood Park (CA)

(73) Assignee: ARIS MD, Inc., Wilmington, DE (US)

( * ) Notice: Subject to any disclaimer, the term of this patent is extended or adjusted under 35 U.S.C. 154(b) by 0 days.

(21) Appl. No.: 16/826,271

(22) Filed: Mar. 22, 2020

(65) Prior Publication Data

US 2021/0058485 A1 Feb. 25, 2021

Related U.S. Application Data

(63) Continuation of application No. 15/058,142, filed on Mar. 1, 2016, now Pat. No. 10,601,950.

(Continued)

(51) Int. Cl.
*G06T 19/00* (2011.01)
*H04L 67/60* (2022.01)
(Continued)

(52) U.S. Cl.
CPC .......... *H04L 67/32* (2013.01); *A61B 1/00009* (2013.01); *A61B 5/021* (2013.01); *A61B 5/024* (2013.01); *A61B 5/14551* (2013.01); *A61B 90/36* (2016.02); *A61F 9/008* (2013.01); *G02B 27/017* (2013.01); *G06T 19/006* (2013.01);
(Continued)

(58) Field of Classification Search
None
See application file for complete search history.

(56) References Cited

U.S. PATENT DOCUMENTS 6,463,168 B1 * 10/2002 Alyassin .................. G06T 7/11
250/201.2
8,311,791 B1 11/2012 Avisar
(Continued)

FOREIGN PATENT DOCUMENTS

DE    10008806 A1   12/2001
WO    2012135653 A1  10/2012
(Continued)

OTHER PUBLICATIONS

International Search Report and Written Opinion of the International Searching Authority, dated Jun. 1, 2016 in App. No. PCT/US2016/020302 (filed Mar. 1, 2016).
(Continued)

*Primary Examiner* — Steven Z Elbinger

(57) ABSTRACT

Data representative of a physical feature of a morphologic subject is received in connection with a procedure to be carried out with respect to the morphologic subject. A view of the morphologic subject overlaid by a virtual image of the physical feature is rendered for a practitioner of the procedure, including generating the virtual image of the physical feature based on the representative data, and rendering the virtual image of the physical feature within the view in accordance with one or more reference points on the morphologic subject such that the virtual image enables in-situ visualization of the physical feature with respect to the morphologic subject.

18 Claims, 21 Drawing Sheets

Related U.S. Application Data

(60) Provisional application No. 62/126,624, filed on Mar. 1, 2015.

(51) Int. Cl.

| | | |
|---|---|---|
| *A61B 5/024* | (2006.01) | |
| *A61B 5/021* | (2006.01) | |
| *A61B 5/1455* | (2006.01) | |
| *A61B 1/00* | (2006.01) | |
| *A61F 9/008* | (2006.01) | |
| *G09B 5/02* | (2006.01) | |
| *G09B 21/00* | (2006.01) | |
| *A61B 90/00* | (2016.01) | |
| *G09B 19/00* | (2006.01) | |
| *G02B 27/01* | (2006.01) | |
| *G09B 23/28* | (2006.01) | |
| *A61B 34/00* | (2016.01) | |
| *A61B 34/20* | (2016.01) | |
| *A61B 34/10* | (2016.01) | |
| *A61B 90/50* | (2016.01) | |

(52) U.S. Cl.
CPC ............ *G09B 5/02* (2013.01); *G09B 19/003* (2013.01); *G09B 21/009* (2013.01); *G09B 23/285* (2013.01); *A61B 34/20* (2016.02); *A61B 2034/101* (2016.02); *A61B 2034/256* (2016.02); *A61B 2090/364* (2016.02); *A61B 2090/365* (2016.02); *A61B 2090/366* (2016.02); *A61B 2090/368* (2016.02); *A61B 2090/502* (2016.02); *A63F 2300/8094* (2013.01); *G02B 2027/014* (2013.01)

(56) References Cited

U.S. PATENT DOCUMENTS

| | | | | |
|---|---|---|---|---|
| 8,504,136 | B1* | 8/2013 | Sun | A61B 5/1079 600/407 |
| 8,831,924 | B2 | 9/2014 | Avisar | |
| 2005/0195587 | A1 | 9/2005 | Moctezuma de la Barrera et al. | |
| 2006/0280348 | A1* | 12/2006 | Smith | G06T 7/0012 382/128 |
| 2009/0018808 | A1 | 1/2009 | Bronstein et al. | |
| 2009/0311655 | A1 | 12/2009 | Karkanias et al. | |
| 2010/0310183 | A1* | 12/2010 | Kendall | G06T 7/42 382/224 |
| 2011/0026795 | A1 | 2/2011 | Leber et al. | |
| 2012/0058457 | A1 | 3/2012 | Savitsky | |
| 2012/0182291 | A1* | 7/2012 | Rawat | G06T 19/20 345/419 |
| 2012/0188352 | A1 | 7/2012 | Wittenberg et al. | |
| 2013/0047103 | A1 | 2/2013 | Avisar | |
| 2013/0230837 | A1 | 9/2013 | Meglan et al. | |
| 2013/0237811 | A1 | 9/2013 | Mihailescu et al. | |
| 2013/0267838 | A1 | 10/2013 | Fronk et al. | |
| 2014/0057236 | A1 | 2/2014 | Meglan et al. | |
| 2014/0071072 | A1 | 3/2014 | Itai | |
| 2014/0343913 | A1 | 11/2014 | Avisar | |
| 2015/0127316 | A1 | 5/2015 | Avisar | |
| 2015/0140535 | A1 | 5/2015 | Geri et al. | |
| 2015/0254422 | A1 | 9/2015 | Avisar | |
| 2015/0351607 | A1* | 12/2015 | Ruppersberg | A61B 5/01 600/473 |
| 2016/0113546 | A1* | 4/2016 | Salahat | G06T 7/136 600/410 |
| 2017/0035517 | A1* | 2/2017 | Geri | G06T 19/20 |
| 2017/0315364 | A1* | 11/2017 | Masumoto | H04N 13/344 |

FOREIGN PATENT DOCUMENTS

| | | |
|---|---|---|
| WO | 2013177520 A1 | 11/2013 |
| WO | 2014134196 A1 | 9/2014 |
| WO | 2015154069 A1 | 10/2015 |

OTHER PUBLICATIONS

Jeffrey R. Korzan et al., "In Vivo Magnetic Resonance Imaging of the Human Cervical Spinal Cord at 3 Tesla," Journal of Magnetic Resonance Imaging 16:21-27 (2002).

* cited by examiner

Surgical Overlay System Diagram

Laparoscopic System Diagram

REALITY-AUGMENTED MORPHOLOGICAL PROCEDURE

CROSS-REFERENCE TO RELATED APPLICATIONS

This application is a continuation of U.S. Nonprovisional patent application Ser. No. 15/058,142, filed Mar. 1, 2016 and entitled "Reality-Augmented Morphological Procedure," which claims the benefit of U.S. Provisional Patent Application No. 62/126,624 filed Mar. 1, 2015 and titled "Augmented-Reality Surgical Operation and Medical Evaluation." This application hereby incorporates by reference, for all purposes, the entireties of U.S. application Ser. Nos. 15/058,142 and 62/126,624.

TECHNICAL FIELD

The present disclosure relates to provision of a medical overlay in virtual reality, augmented reality, projected or other virtual space.

DRAWINGS

The various embodiments disclosed herein are illustrated by way of example, and not by way of limitation, in the figures of the accompanying drawings and in which like reference numerals refer to similar elements and in which.

DETAILED DESCRIPTION

Figure 1:
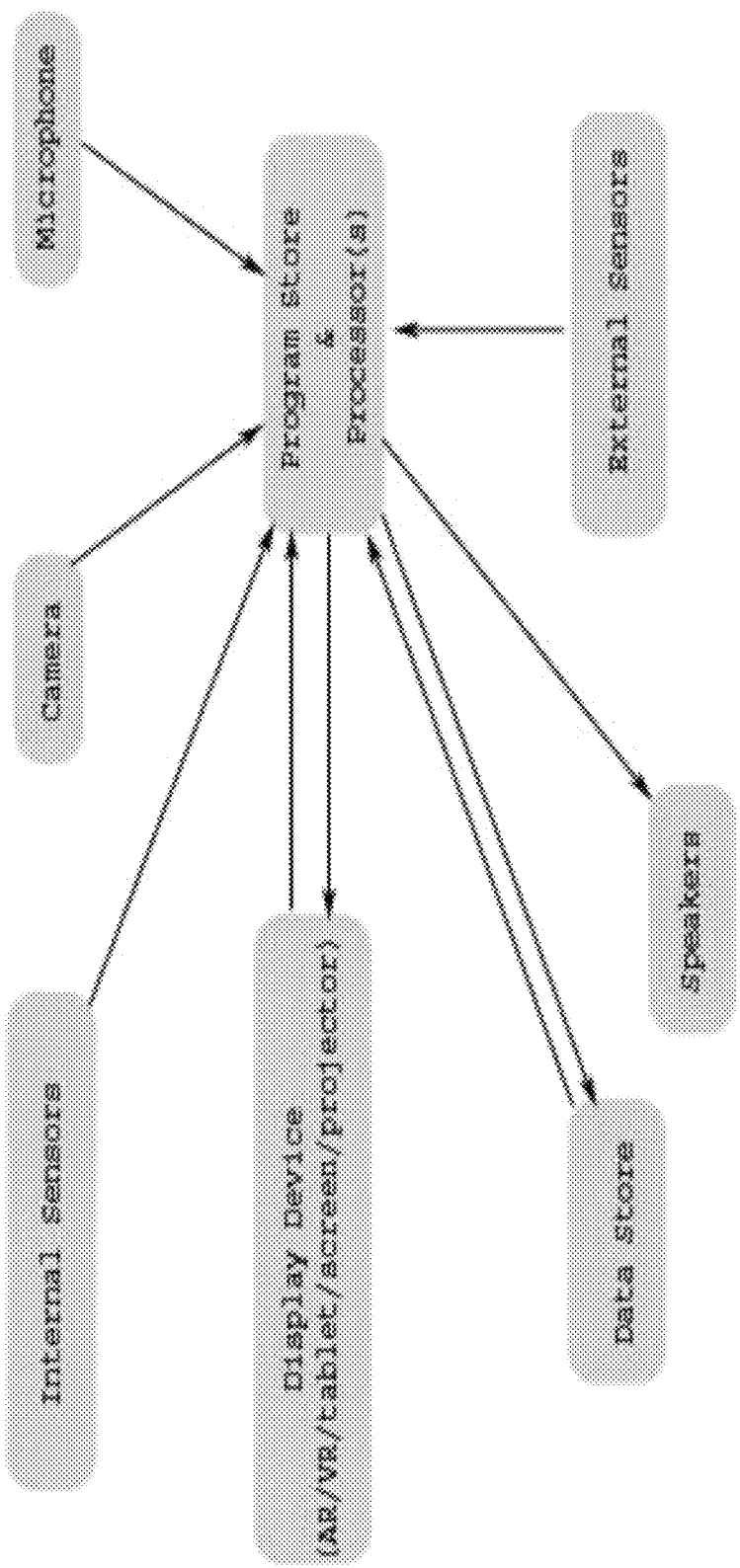
FIG. 1 illustrates an exemplary surgical overlay system diagram.

Methods, systems and system components are disclosed in various embodiments for viewing and accurately locating patient organs, arteries and other features prior to and during surgery, thereby reducing morbidity and mortality due to surgical error associated with variance in patient feature location. In a number of embodiments, imaging data is interpreted into an Augmented Reality ("AR") or Virtual Reality ("VR") view of a patient, to be shown to a doctor, surgeon or other medical practitioner during a procedure in order to enhance the accuracy and efficacy of the procedure. Methods and apparatuses interpret imaging data into an AR or VR view of a subject for use by other users including, but not limited to, insurance auditors, non-surgical physicians, nurses and legal professionals.

Methods and apparatuses for providing a heads-up display ("HUD") displaying both augmented reality ("AR") path data and camera imagery for laparoscopic cameras during medical procedures are also disclosed. In a number of embodiments, locations of the laparoscope camera and/or carrier tube are tracked during laparoscopy, with transmission of the camera image to a device, and overlay of the location and path data of the laparoscope in augmented reality.

Various techniques and apparatuses for training and testing of surgical and diagnostic skills using Augmented Reality ("AR") or Virtual Reality ("VR") and display of patient morphological data gathered by Magnetic Resonance Imaging ("MM") are also disclosed. In a number of embodiments, patient morphological data (e.g., composed from an Mill, CT scan, x-ray, or any other patient data source) is displayed to a practitioner/trainee and further enhanced through AR or VR to simulate a variety of conditions for testing and training.

A "procedure" is defined herein to include, without limitation, any surgical, diagnostic, chiropractic, physiotherapeutic, rehabilitative and/or other task performed on a corporeal body.

A "practitioner" is defined to include, but is not limited to, any agent performing a procedure.

"Morphologic subject", "morphological image", "morphological data", "morphology" and other variants are defined to include, but are not limited to, Magnetic Resonance Imaging ("MM"), Computerised Tomography ("CT"), Computerised Axial Tomography ("CAT"), Positron Emission Tomography-Computed Tomography ("PET-CT"), optical coherence tomography ("OCT"), swept source optical coherence tomography ("SS-OCT"), optical coherence tomography angiogram ("OCTA"), ultrasound, X-Ray, Nuclear Magnetic Resonance, mammography, angiogram, pelvic ultrasound, digital photography, camera photography, atom probe tomography ("APT"), computed tomography imaging spectrometer ("CTIS"), laser scanning confocal microscopy ("LSCM"), Cryoelectron tomography ("Cryo-ET"), electrical capacitance tomography ("ECT"), electrical resistive tomography ("ERT"), electrical impedance tomography ("EIT"), Electron tomography ("ET"), laser ablation tomography ("LAT"), magnetic induction tomography ("MIT"), muon tomography, corneal topography (videokeratography), neutron tomography, acoustic tomography, optical diffusion tomography ("ODT"), optical projection tomography ("OPT"), photoacoustic imaging ("PAT"), positron emission tomography ("PET"), quantum tomography, single photon emission computed tomography ("SPECT"), seismic tomography, thermoacoustic imaging, ultrasound-modulated optical tomography ("UOT"), skin topography, or arteriography.

An AR device is any device comprised of a computer controlled display capable of displaying either a transparent image atop real world data, such as glasses with an embedded transparent display mechanism, or a device capable of displaying a composite image from a camera or other imaging source coupled with overlaid three dimensional data.

A VR device is any device comprised of a computer controlled display which covers the users' vision and immerses them in a virtual environment.

I. Visual AR/VR Medical Overlay

Surgical Overlay

One embodiment relates to a method for displaying surgical targets and other pertinent medical and/or anatomical data in an augmented or virtual reality surgical environment.

When performing a surgery, there exists a target location and/or anatomical part of the patient. By displaying a three dimensional rendered image, the efficacy of the surgery can be increased, while reducing patient morbidity and mortality. The practitioner can optionally control the rendered image as described below.

In augmented reality, the rendered image is seen by the user or users as a three dimensional model of the patient's morphology overlaid atop the physical patient. In the case of virtual reality, the patient morphology becomes the three dimensional model for the patient, and is treated as the patient for the intended applications of the invention. In a projection environment, the rendered image data is projected onto the subject using a projector or projectors mounted with a view of the patient. Multiple projectors are used to prevent the user or users from interrupting the image, as well as to allow for a three dimensional image to be presented.

The system is minimally comprised of a display device, the medical overlay software, patient morphology data, and a camera. In this minimal embodiment, the display device shows the image from the camera, and the software interprets the image and places the patient morphological data in the correct location. Using the image from the camera, the software updates the rendered image as described below.

In another embodiment [FIG. 1], the system is comprised of a pair of augmented reality glasses, tablet, display screen, virtual reality glasses or head-mounted display, sensors for tracking movement of the AR or VR device, the medical overlay software, a camera, an audio capture device, sensors for positional tracking of specific objects such as scalpels, hands or other instruments, optionally speakers, and/or a data store for the patient morphology which can be either pre-loaded onto the device or transferred by network on demand. A projector can be used in place of the AR or VR display.

Figure 2:
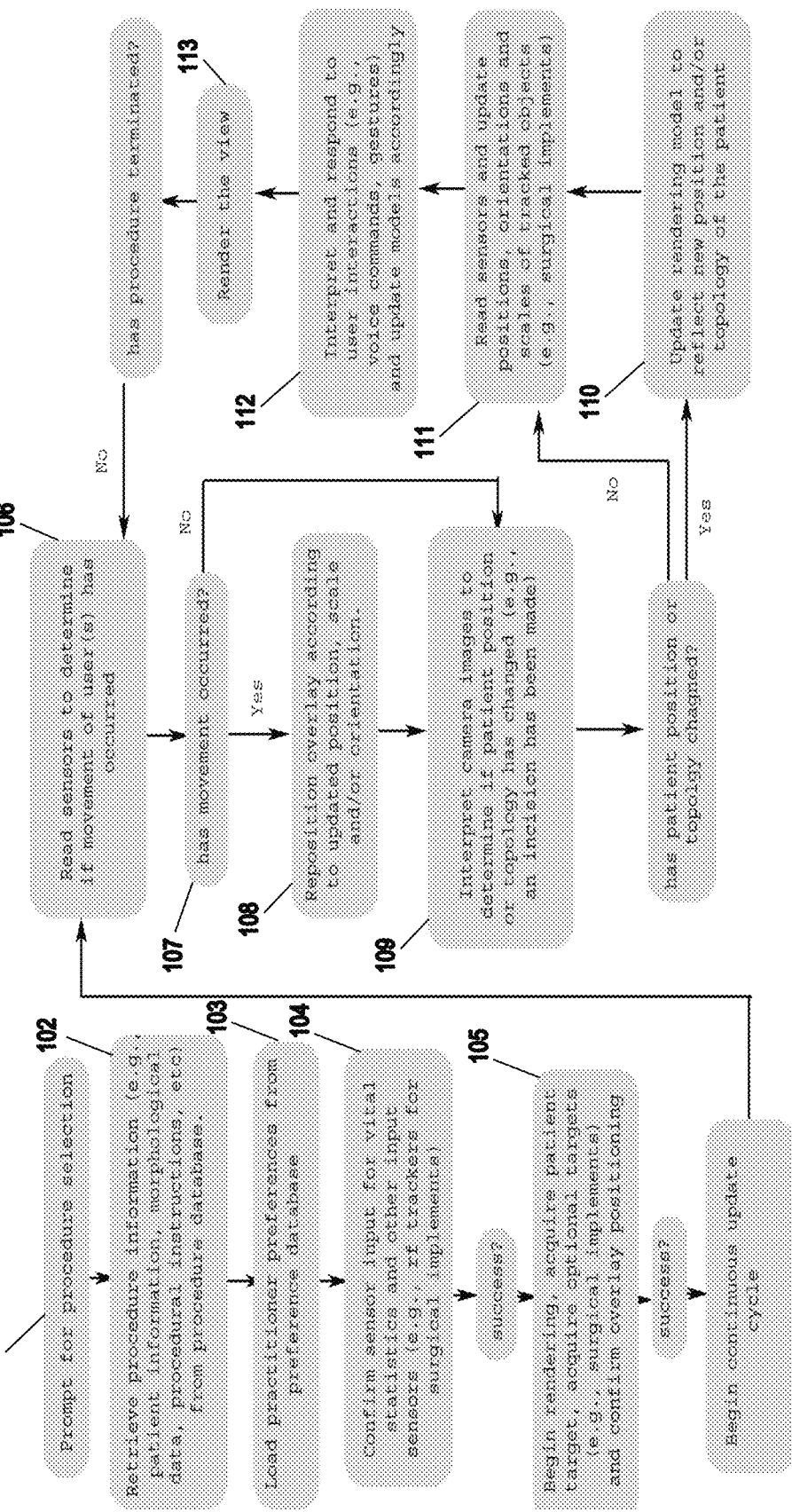
FIG. 2 illustrates the surgical overlay program flow.

When the system is initialized [FIG. 2, 101], the user first selects the procedure to be performed. The list of selectable procedures comes from a database of currently prepared patient procedures. The data retrieved from the database is herein referenced as "procedural data", which can include, but is not limited to, the patient morphological data, patient information, procedural instructions, procedure time/date, and/or procedure location.

The procedural data is then loaded from the database and stored in the program store being used for the execution of the system using a data reception interface [FIG. 2, 102]. This can be, but is not limited to, random access memory ("RAM"), a solid state drive ("SSD"), a secure digital card ("SD card"), and/or hard disk drive ("HDD") accessible to the system.

Optionally, the preferences of the current user or users are then retrieved from a database of user preferences [FIG. 2, 103]. The preferences loaded are herein referred to as "practitioner preferences" and can include, but are not limited to, display brightness, HUD transparency, HUD element location preferences, audio volume and/or preferred input method.

The system is then connected to sensor inputs to be monitored and/or tracked during execution. These sensors can be, but are not limited to, pulse monitors, blood pressure monitors, oxygen saturation monitors and/or wireless sensor such as, but not limited to, radio frequency ("RF") positional indicators. Sensor inputs are then verified to ensure that they are being correctly read [FIG. 2, 104]. The system displays to the user(s) the currently read value from each sensor in turn, and the user(s) then confirm that the value is correct. System execution is halted if the verification fails, unless user(s) specifically override the verification process.

Following verification, visual targets are then acquired by the system, the patient identity is confirmed and the rendered image position, orientation and/or scale are verified [FIG. 2,105].

In order to visually track surgical instruments and other objects in the augmented reality space, the user can hold the instrument in a location visible to the camera and request that the software identify the instrument. Through user interaction it is determined whether the software has correctly identified the implement. When the user is satisfied that the implement is being correctly identified, they then indicate through a command—vocal or other user interface method—to track the identified instrument. Alternatively, a tracking marker can be attached to the instrument to be tracked and shown to the camera, then indicated to the software through a user interface to begin tracking the marker. Alternatively or additionally, one or more radio-frequency (RF) based tracking elements may be attached to or built into the instrument and engaged (e.g., Bluetooth pairing or other one-way or two-way communication link), at which point the software will begin tracking the tracking element(s).

Confirmation of the patient is done in two ways. Firstly, the patient's information is encoded in the morphology data. The user compares the information in the morphology to the information associated with the patient, whether on a hospital bracelet, clipboard, and/or other standard method of identifying patients. The morphology will also match only the correct patient, and therefore the rendered image will appear only when the correct patient is visible to the system.

The rendered image as a whole is anchored to the location of the patient. Herein, rendered image anchoring refers to positioning features of the rendered image, such as, but not limited to, detected features and/or perimeter location, and thus the rendered image as a whole such that the rendered image features are fixed in position relative to the positioning features. Feature detection, perimeter detection, and/or point cloud mapping are used in conjunction to determine an accurate three dimensional location, scale and orientation of the patient. These metrics are updated continuously as the program executes, to ensure that the rendered image is always anchored correctly. Markers can also be used, such as surgical tattoos or other visual markers, to ensure the correct anchoring of the morphological model.

Prior to commencing the procedure, the user or users do a walk around of the patient to ensure that the rendered image is properly sized and aligned to the patient. If the alignment is incorrect, the user(s) can correct the alignment using any method of user input available on the device.

The three dimensional rendered image is rendered on the device, which in the case of augmented reality glasses could be a transparent screen embedded in the glasses themselves. In the case of virtual reality, the rendered image is rendered on the non-transparent VR display. In the case of a projection system, the rendered image is projected onto the patient from any number of projectors mounted for that purpose. Multiple projectors allow the projection to be unobstructed by movement of the user or users.

During the procedure, the rendered image is continually updated to display the current morphology of the patient [FIG. 2, 106]. As a surgeon makes incisions and opens portions of anatomy, the rendered image is updated in real time to present a progressively deeper view and rendered image with respect to the patient morphology. This depth-tracking operation of the display can also be overridden by the user or users using gestures, voice commands or any other form of user input. The user(s) are also able to individually select and manipulate portions of the displayed morphology, such as removing an organ from the model to view behind or below the organ or to view the organ from various perspectives and proximities (orbiting, panning, zooming). For example, the user(s) can also rotate and reorient the portion that has been removed to see it from different angles, as well as adjusting the display depth to see inside the segment. All of these viewing controls may be effected through user input such as gestures, voice commands, swipes, taps, mouse-motion, keyboard control, etc. The user(s) are also able to zoom in on the model in any portion, whether it be a portion which has been removed from the primary morphology or a portion of the primary morphology or all of the morphology itself.

Relative movement between the patient and system user(s)—and thus actual or perceived movement of the markers used to anchor the rendered image—may be detected in several ways [FIG. 2, 107]. One such method is the frame offset method described below. Supplementary information is also provided using the positional sensors in the augmented or virtual reality device (e.g., in the AR/VR goggles, display-shield or other rendering device). In the case of a projection system, the projector is in a fixed position and therefore supplementary information is unavailable. As the user(s) move, his or her location in three dimensional space is updated in the software, which in turn updates the visible rendered image model or virtual model [FIG. 2, 108]. The model is also adjusted based on positional changes in the patient [FIG. 2, 109]. Transformation of the location, orientation and/or scale of the morphological data is done using quaternion and/or matrix operations to transform, translate and/or rotate the points in the data set [FIG. 2, 110]. As the patient moves, the morphological data is transformed to match the adjusted positions of the patient, as explained in an example below.

The positions of any tracked objects are then determined in three dimensional space, and their location for the purpose of the rendering image are updated and stored [FIG. 2, 111]. User input, as described above, is then processed [FIG. 2,112]. Once input has been processed and the rendered image has been updated, the view is rendered using a rendering engine [FIG. 2, 113].

While using a surgical overlay, audio and/or visual cues are given to the surgeon if they are approaching an area which has either been noted as an area to avoid or use caution. For example, if a surgeon is performing surgery on the intestinal tract and the scalpel is getting close to the patients' bowel, a visual and/or auditory proximity warning may be rendered to inform the surgeon that they have come too close. The warning could, for example, be a red area displayed in augmented reality. A recorded warning or warning sound could also be played.

Anatomical Overlay

Another embodiment also relates to a method and apparatus for providing an anatomical display in virtual reality, augmented reality or other virtual space.

Anatomical diagrams, anatomical models and cadaver dissection are the de facto standard for teaching anatomy to medical students. By providing anatomical data in a virtual space, anatomy can be learned in three dimensions. This anatomical model can also include notes to be displayed to the user or users. The model is not limited to humans, and can also be used for veterinary purposes using anatomical models of animals and other living organisms. The model can also be interacted with by the user or users, allowing for dissection and manipulation of individual components of the model. Selection of specific parts of the model can be made by any method of user input, including but not limited to voice, gesture and device input. More details of a selected model can be made available to the user(s) visually or aurally.

In augmented or virtual reality, three dimensional anatomical models are displayed in a location where no actual model exists. In augmented reality, the model can optionally be overlaid over a marker or other positional indicator, or even at a fixed location relative to the user or users which may contain physical objects. The model is presented in three dimensions, and the display of the model can also be manipulated as outlined below.

An anatomical model is displayed in augmented reality using a system comprised of an augmented reality device such as a tablet, glasses, projector(s) or other display medium, a camera, sensors for tracking positional movement of the camera and/or user(s), optionally speakers and an audio capture device for audio feedback and input respectively and a data store for the patient morphology which can be either pre-loaded onto the device or transferred by network on demand.

Annotations are also optionally displayed to the user or users, along with the ability to open detailed descriptions of individual anatomical components. While examining or dissecting the anatomical model, the user or users are able to manipulate anatomical components and move them away from the main model, examining them in detail in three dimensions. The user or users are also able to zoom in on particular sections or on the entire model to have a closer look. The user or users are also able to rotate and reorient the model, as well as individual sections of the model.

Users are able to dissect the virtual anatomical model using user input controls. The model can also be dissected using surgical instruments, either real or virtual. Virtual instruments are pre-created and instantiated within the virtual space using any common user input method. Real instruments can be tracked and used as described above. As the user or users dissect the virtual model they see each individual component of anatomy, and are able to dissect the individual components. Users are also able to reverse their actions using any method of user input to undo their actions sequentially. The model can also be reset to the original position at any time using a command issued by user input.

The user or users are able to move around the virtual model in three dimensions. The model is fixed to a point in three dimensional space, selected when the model is first initialized. The model can be moved from this space with user interaction, but is otherwise anchored in place. The location is determined using a combination of the frame offset methodology described below, as well as positional information given by the device and/or camera. In augmented reality, the user or users are able to navigate around the model by moving their body in relation to the virtual model. In virtual reality, the user or users are able to move through the virtual space using commands issued by user input, in conjunction with head tracking and any other available positional tracking information.

Laparoscopic Overlay

Another embodiment relates to a method and apparatus for providing a visual display of laparoscopic information in virtual reality, augmented reality, or other virtual space.

Laparoscopic procedures involve a surgical camera (laparoscope) and surgical tools. By displaying radiological images overlaid over a patient in augmented or virtual reality, surgical targets, such as cancerous growths, can be more accurately targeted and located by a practitioner. The location of the laparoscope and surgical tools can also be displayed. The historical location of the laparoscope and surgical tools can also be shown as path data. A practitioner could also take notes, either vocally or using pre-determined commands, gestures or other pre-determined user interface options.

In a laparoscopic surgery, the surgeon is unable to see the actual location of the laparoscopic devices. The augmented reality device displays the current location of the laparoscopic heads, the historical locations (path) of the laparoscopic heads, and/or a HUD [see below] which displays the laparoscopic camera view. The device also displays (optionally) morphological data as explained above.

Figure 3:
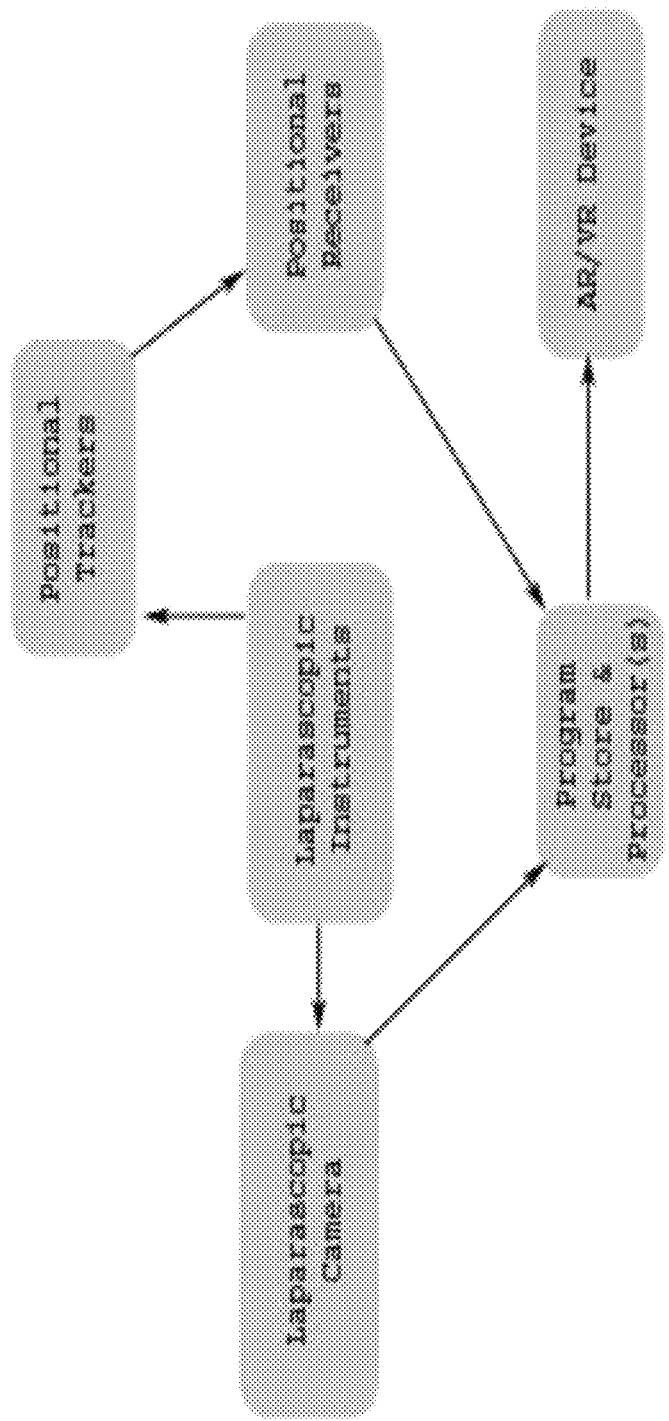
FIG. 3 illustrates an exemplary laparoscopic system diagram.

The laparoscopic overlay [FIG. 3] is comprised of a laparoscopic surgical setup, augmented reality or virtual reality device (including camera and positional tracking), software, positional trackers, positional receivers and an interface between the receiver and augmented reality device. The positional trackers are paired with the receiver(s), and attached to the ends of the laparoscopic instruments. The receivers are connected, preferably wirelessly, to the augmented reality device. The laparoscopic camera is connected (preferably wirelessly) to the augmented reality device.

Figure 4:
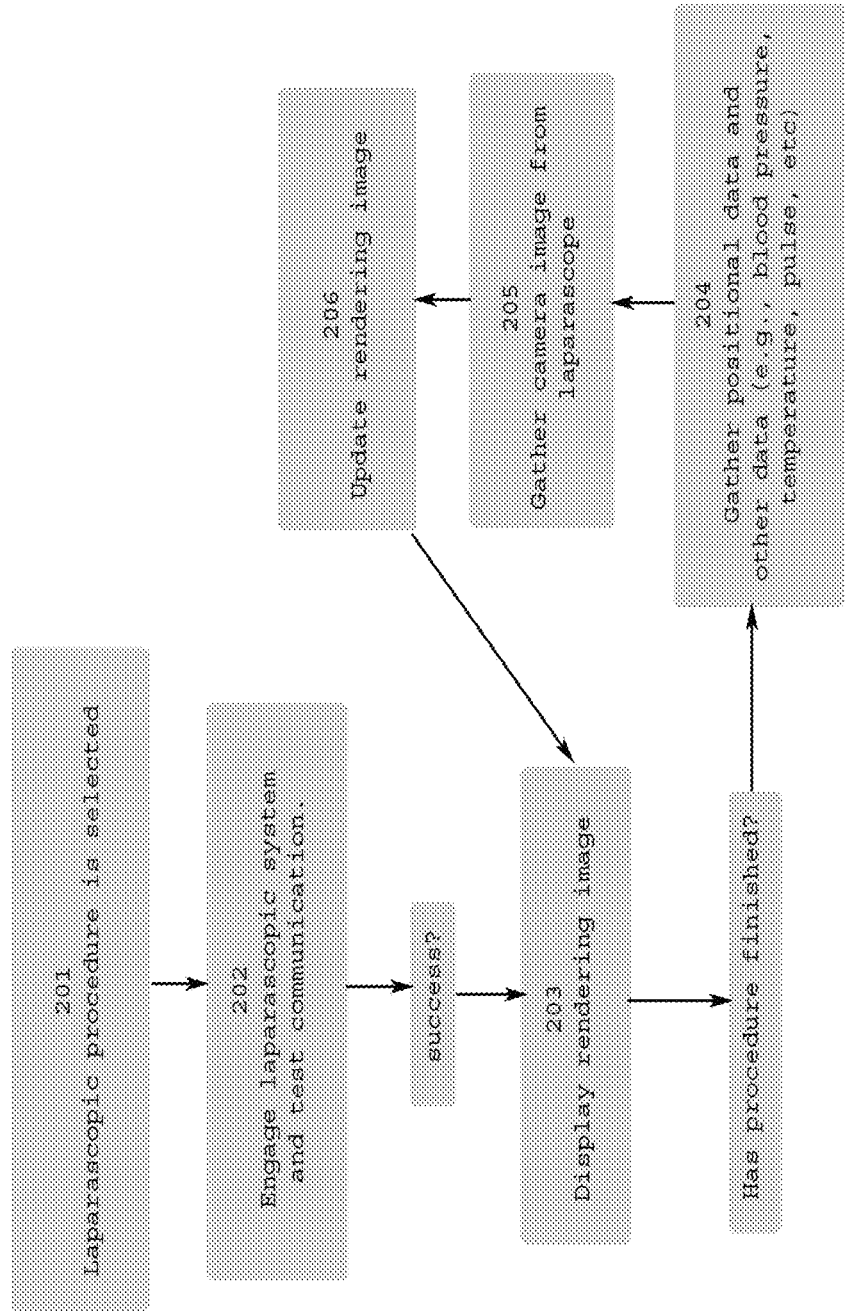
FIG. 4 illustrates the laparoscopic program flow.

When the laparoscopic procedure has started, the system is engaged [FIG. 4, 201]. The transmitters are then tested to verify that communications are correct between the transmitters, receivers and software [FIG. 4, 202]. A rendering image is then displayed showing the initial positions of the transmitters, as well as the initial camera view from the laparascope [FIG. 4, 203].

The positions of the laparoscopic heads are transmitted at regular intervals, as quickly as the slowest component in the system is able to handle [FIG. 4, 204]. In order to maintain accurate and current positional locations for the trackers, the tracker and receiver operate at as rapid of a frequency as they are able. The augmented reality device then requests from the receiver an updated position as often as it is able to display it. Only the most recent positional data is returned to the augmented reality device for display. The image from the laparoscopic camera is also requested [FIG. 4, 205].

The rendering image is updated using the current and historical positions of the laparascope trackers, as well as the camera image [FIG. 4, 206]. The current positions are displayed to the user or users in augmented reality, as well as the historical positions. This allows the user(s) to see both the current location and the track taken to arrive at the current location. The camera view is also displayed in a HUD (see below). This process repeats [FIG. 4, 202] until the procedure has finished.

Another embodiment also relates to a method for using augmented reality in laser eye surgery.

For example, laser eye resurfacing is a process of improving a patients vision by resurfacing the cornea of an eye to more accurately focus light on the patients retina.

Another embodiment is comprised of an augmented reality display, camera or other imaging device, laser, and/or a cutting tool [laser, mechanical, etc.]. The surface of the cornea is scanned, and a model is created in AR. This AR model is used to assist in guiding the surgeon while using a laser to alter the surface of the cornea. The AR model is displayed either as an overlay over the actual cornea, or as a display in a HUD (see below).

Real-Time/Head-Up Display

During medical procedures, patient vital statistics, imaging, and other patient data are often required for consultation. A real-time updating display of the aforementioned data allows a practitioner to focus on the patient or task at hand without having to consult devices or paper sources to monitor or retrieve information. A range can also be set to trigger an alarm should a vital leave the acceptable range.

For example, a surgeon performing an appendectomy with a heads-up display (HUD) could have a display of patient vital statistics shown in augmented reality, allowing the surgeon to focus on the surgical procedure without having to look away in order to ensure that the patient's blood pressure remained stable.

The HUD is comprised of an AR device or other display medium and source inputs, such as vital signs monitors. The HUD is configured automatically, in advance, or by user interaction to select the type of source data to be displayed. The data is then displayed in a location determined automatically, in advance, or by user interaction. The transparency (alpha channel value) of the HUD elements can also be adjusted to allow for better visibility of the HUD item or underlying detail.

Once the source inputs have been connected to the HUD, the values are read at regular intervals and the HUD elements are updated with the new values.

Another embodiment relates to a method and apparatus for displaying a heads-up display (HUD) composed of two and/or three dimensional images superimposed on the environment.

A heads-up display can be used for a large variety of purposes. In a virtual environment, a HUD gives a viewer consistent information which remains visible regardless of the viewing context. This data can be configured to show different information based on pre-set conditions, user preferences, environmental factors, and/or contextual data.

For example, a doctor seeing patients could have a HUD displaying patient information triggered by facial recognition of the patients. Additionally, for each patient, the doctor could configure which data would be most valuable to see, and have that specific data displayed in the HUD either for a single visit or on a long-term basis.

Various embodiments disclosed herein relate to a method for providing an augmented or virtual reality surgical overlay, comprised of elements including, but not limited to, heads-up-display (HUD), medical imaging display, vital statistics display, patient information display, procedural information and other data.

The heads-up display is created using two or three dimensional images or models, with adaptive portions related to the data to be displayed. In the case of vital statistics, the data is streamed from a medical device connected to the subject. The data is then fed into the software where it's interpreted based on the information to be displayed, and displayed as appropriate. For a patients O2 saturation, for example, the raw data expressed as a percentage can be converted to an integral percentage number for display in the HUD.

In another embodiment, the HUD can be replaced with another viewing medium such as, but not limited to, an LCD or CRT screen. This view does not necessarily include a virtual space.

Figure 5:
FIG. 5 illustrates an exemplary head-up display (HUD) with two- and three-dimensional elements.

FIG. 5 shows a sample HUD configuration. The four vital signs being monitored, temperature, oxygen saturation, pulse rate and blood pressure are shown in the top left, top right, bottom left, and bottom right corners respectively. These displays are transparent and are in fixed positions such that as the user or users turn their heads, the vital signs remain in a constant position relative to the camera.

Similarly, medical images in formats recognized by the software, including, but not limited to, DICOM, Jpeg, png, bitmap, raw, and other similar formats, can be overlaid as a part of the HUD to allow the practitioner to see them in virtual space at all times.

Patient information and vital statistics can also be displayed in a similar manner, having been loaded from a medical database or other pre-existing source. Data can also be manually entered.

Procedural directions and information are also available from pre-created sources. These procedures and methods can be stepped through using various forms of user interaction such as voice control, gesture control or other control method.

Figure 6:
FIG. 6 illustrates concurrent HUD display of an exemplary image and procedural step.

FIG. 6 shows a HUD identical to FIG. 1, however on the left below the temperature stats a guide can be shown giving instructions to the user on how to perform a procedure. As each step is completed, the guide is updated either automatically or with user interaction.

Another embodiment relates to a method for displaying surgical targets and other pertinent medical and/or anatomical data in an augmented or virtual reality environment.

The target area can be selected through a three dimensional virtual space. Target areas can also be selected by a practitioner on a patient using an overlay. Target areas can also be selected using a pen, finger or other positional device. The targets can also be displayed on a conventional display, such as but not limited to, an LCD or CRT screen. Positional tracking information sent from a surgical implement or other tracking method can be used to identify to the practitioner where the implement or tracker is relative to the targeted location on the CRT screen. Positionally tracked objects or implements can be seen in augmented reality, even when obscured by real world objects. For example, the blade of a scalpel while making an incision is visible in augmented reality, despite being obscured by the flesh being cut.

Figure 7:
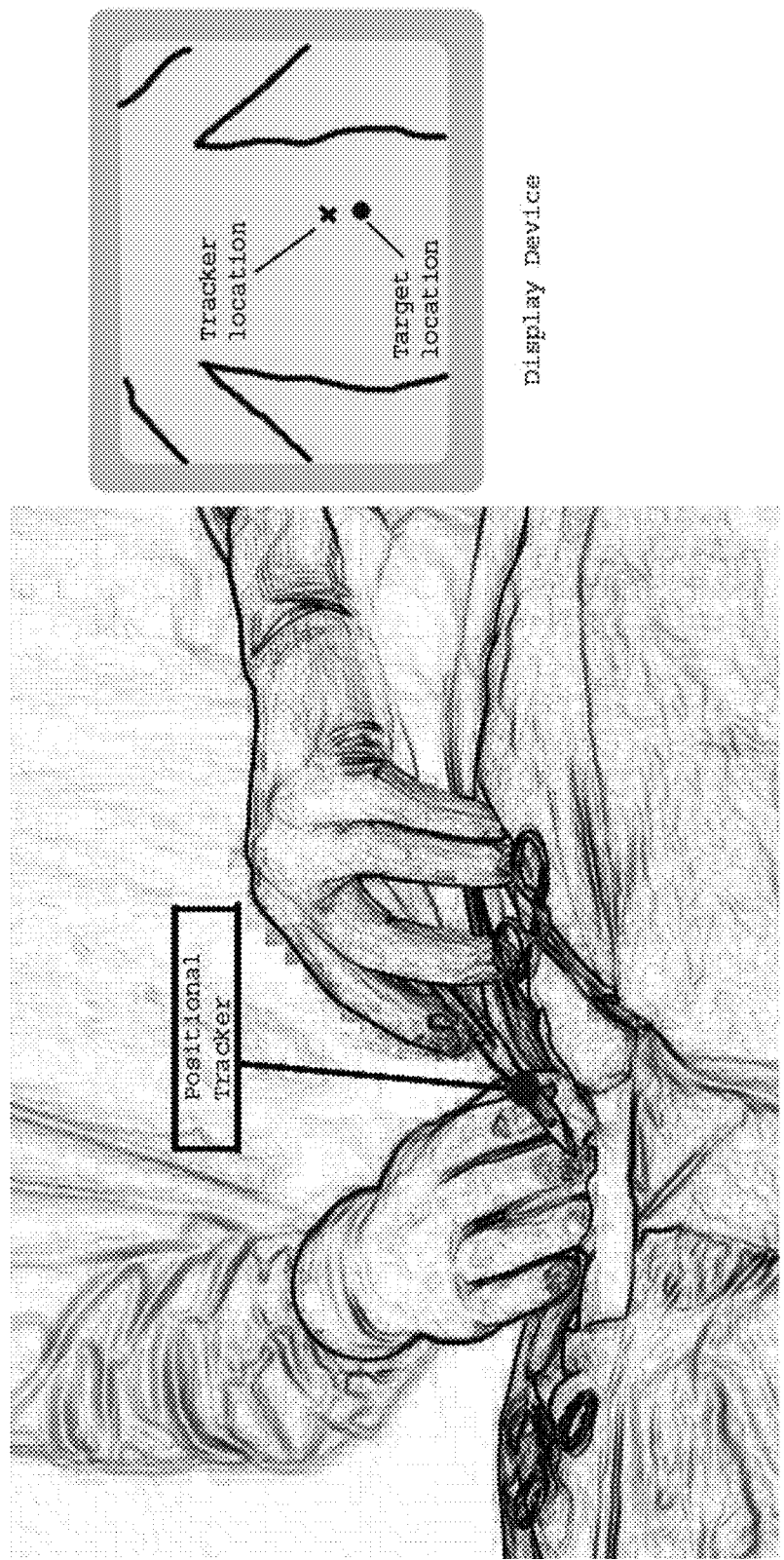
FIG. 7 illustrates an example of a doctor using a scalpel with a tracker and a monitor.

FIG. 7 shows a scalpel equipped with a positional tracker (left) being used by a surgeon. On the right, a display device is shown with a mock up of a patients morphology. The X on the display device represents the current location of the scalpel, while the circle represents the surgical target location. By looking at the display device, the surgeon can determine when they've reached the correct location to begin their incision.

For example, a surgeon reviews an MR image of a patients abdomen. The target location for an abdominal surgery is identified from the image. Using a diagram of the patient, the surgeon marks the target area. During surgery, the diagram is displayed on a monitor next to the patient. A positional tracker attached to a scalpel displays the position of the scalpel relative to the patient on the monitor as well. When the position of the scalpel matches the position of the target, the surgeon is able to see on the monitor that the positions are the same. This indicates to the surgeon that the right location has been found to begin the surgery.

In another example, a surgeon performing surgery to remove a tumour on a patients' heart can separate the patients heart from the body in augmented reality, move the heart away from the patient, and inspect the heart and associated tumour in three dimensional space. This allows the surgeon to better assess the location of the tumour, as well as to plan the best route of access for it's removal. This will allow for more surgical accuracy tailored to individuals. This view can also be shared via network with other users for consultation or other uses.

In another example, an instructor uses a positional tracker attached to a pen or other implement to test students' knowledge. The instructor has previously identified a target for a surgical procedure, and the students are asked to locate the target using the implement. The instructor, wearing a pair of augmented reality glasses, can view the proximity of the students' answer to the actual target. In another version of this example, the student could be shown a radiological image and asked to identify the correct target location from the image.

In another example, a physiotherapist uses morphological images to display a spinal injury. Using this overlay, the physiotherapist is able to accurately assist the patient without causing further injury or damage to the spine.

In another example, a patient bends their right arm during a procedure for which a rendered image is used. The morphological source data is then updated to reflect the new position of the bent arm. The camera image is analyzed to determine the direction and degree of the bend in the arm at various points. Using this direction and degree, the morphological data is updated to reflect new positions for each point that has moved using standard quaternion and/or matrix based transformation methods.

Another embodiment relates to a method for providing an augmented or virtual reality surgical overlay for laparoscopic procedures, comprised of elements including, but not limited to, mapping of laparoscopic device path, display of laparoscopic device position, display of laparoscopic imaging data, and/or system for taking notes generally and related to specific points.

Laparoscopes are currently equipped with a camera for viewing the inside of a patient or other area in order to perform surgery non-invasively. By mounting a transmitter on the end of the laparoscope, and used in conjunction with a receiver connected to software, the location and historical path of the laparoscope can be tracked and displayed in virtual space. The transmitter can be using any frequency allowable within a surgical environment, such as, but not limited to, RF, Bluetooth, or WiFi.

The data from the camera can also be read and displayed in real time in a virtual space, either as a primary display or a HUD. Having a display in view during the entire procedure allows for reduced morbidity and mortality during the procedure.

Figure 8:
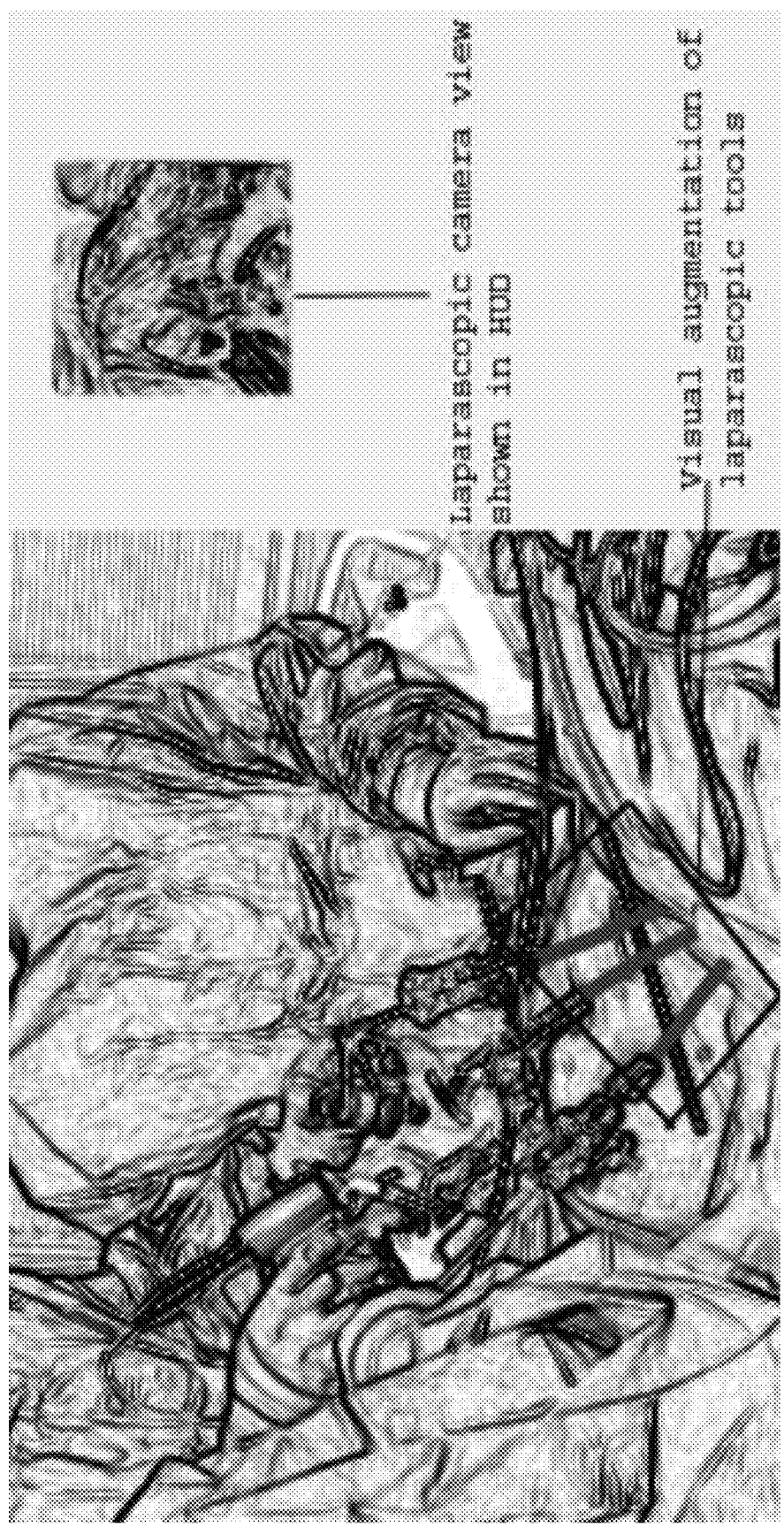
FIG. 8 illustrates an exemplary laparoscope path display and HUD camera.

FIG. 8 shows a laparoscopic procedure in progress. On the left the augmented reality paths and tips of the laparoscopic instruments can be seen. On the right the camera view from the laparascope is shown, which would be visible in the HUD of the surgeon or other user.

Additionally, the practitioner can make notes using a user interface comprised of voice recognition, gesture recognition, and/or other forms of inputs. A practitioner can use a predetermined gesture to identify the location where they would like to annotate. Once the gesture has been recognized, they can then speak the note they wish to take, which will be interpreted by well known methods of voice recognition and converted to text to be displayed in the HUD. These notes are also recorded for future reference.

For example, when planning for an appendectomy, a surgeon reviews the patients model. While inspecting the model and planning a route for the surgery, the surgeon notices that the patient has a postilieal appendix. Due to the position of the appendix, the surgeon makes a note on the model to be cautious of the ileum, with the hope of reducing the risk of accidental damage to the ileum.

For example, in laparoscopic cholecystectomy (surgical removal of the gall bladder), a laparoscope is used to locate the gall bladder for removal. The display from the laparoscope is traditionally shown on a screen next to the surgical area, and the surgeon is unable to see the laparoscope's location or path. Further, the surgeon is unable to focus on the laparoscope output while looking at the patient. Using augmented reality, the laparoscope position and its path through the patients body can be displayed directly on the patient's body. The camera view from the laparoscope can also be shown in the HUD, allowing the surgeon to see both the patient and the camera simultaneously.

Another embodiment relates to a method for displaying a heads-up display (HUD) in augmented or virtual reality composed of two or three dimensional images superimposed on or integrated into the environment being viewed.

A HUD is used to display data to a user in a virtual space. The elements of the HUD can be either fixed positionally to the view of the user, to locations in the real or virtual environment, or a combination of both. For example, in displaying patient data to a user, some elements of the HUD could be fixed to the location of the patient (such as heart rate, blood pressure), while other elements could be fixed to the view of the practitioner, such as radiological images, patient information, or procedural notes.

Figure 9:
FIG. 9 illustrates exemplary HUD elements attached to a patient and an exemplary view presented in the HUD.

FIG. 9 shows two separate HUD elements. One, a pulse rate for the patient, is anchored to the patient's location and remains in the same place in three dimensional space as the user moves about. The second, which includes the patient's name, age and blood type, is fixed to the bottom left corner of the view.

For example, a doctor doing rounds between hospital rooms can have a HUD for display of patient vital signs. As the doctor passes from one patient room to another, the HUD updates with the patient the doctor is currently visiting.

In another example, during anaesthesia, a patient must be monitored constantly to ensure that their vital signs remain stable and in an acceptable range. Using an augmented reality device connected to vital sign monitors, the person monitoring the patient can keep the vital signs in view at all times using an augmented HUD. This allows the monitor to perform other tasks while continuing to monitor the patient under anaesthetic. Multiple patient vital signs can also be connected to a single augmented reality device, allowing a single monitor to watch over multiple patients under anaesthetic.

In another embodiment, first responders (e.g. EMT) can use a virtual space device programmed with early life saving processes. A patients vitals can be streamed to the device, and based on symptoms a protocol is initiated to provide step by step life saving steps to the first responder.

In another embodiment, a nurse or resident on call has a virtual space device connected to patients' emergency buttons. When the emergency button is pressed, the patients vitals and location are connected to the device. The device can also be connected to the physician in charge of the patient, who may be present in hospital or on call. The nurse, resident or physician can then communicate with the patient and each other to determine the correct steps to ensure the safety of the patient.

For example, a nurse watching a ward floor at night is at a desk outside the patients' rooms. A HUD displayed in augmented reality is shown to the nurse while filling out paperwork. A patient presses the emergency button. The vitals for the patient are immediately displayed in the HUD, and the nurse sees that the patient is tachycardic. The patient history in the HUD shows no history of tachycardia or related conditions, so the nurse initiates a call to the doctor on call through the augmented reality device. The doctor, who is at home, is able to view the situation through the camera on the nurse's augmented reality device and walk the nurse through the steps of stabilizing the patient while travelling to the hospital.

Another embodiment relates to a method for using augmented reality in laser eye surgery.

By using an augmented reality overlay in a laser eye surgery procedures, better accuracy can be given to the surgeon. The eye can be scanned and the surgical target overlaid over the eye. This target can also be manipulated as described below, including the ability to move it to another location, zoom, rotate, and otherwise manipulate it for closer inspection and note taking.

For example, the cornea of a user can be scanned by high definition camera or other means in a LASIK surgery. The desired shape of the cornea is compared to the scanned cornea's surface. An augmented reality overlay of the differences is shown on the cornea of the subject during resurfacing, with the virtual object being updated as the surgeon reshapes the cornea. This allows the surgeon to be certain of correctly resurfacing all portions of the cornea during the procedure, reducing surgical error.

In another example, the back of a patient's eye is scanned and mapped to find a tear in the retina. A small tear is located and processed into an augmented reality morphology model. This morphological model is superimposed over the patients eye, showing the practitioner accurately the location of the retinal tear. The tear can then be repaired easily and safely using an argon laser.

Another embodiment relates to a method for analyzing radiological images with a moving patient for diagnostic purposes.

Using radiological images taken at different points of motion can show changes in joint position and possible fluid buildups, for example. This can also be used to diagnose conditions such as arthritis.

II. AR/VR-Assisted Medical Training/Learning/Simulation/Testing

Another embodiment relates to a method for combining gross anatomy with problem based learning (PBL).

Gross anatomy and PBL are two different methods used in the teaching of anatomy. By combining both methods, an enhanced understanding can be had by the student.

Another embodiment relates to a method and apparatus for providing medical simulations in virtual reality, augmented reality, or other virtual space.

Medical and diagnostic training is primarily provided through classroom learning, followed by a period of residency where a student learns by seeing real patients. The ability to train in surgical and diagnostic procedures, however, is currently lacking. Using simulations in virtual space, a student can receive hands-on practice without risk to patients, and with the ability for an instructor or peer to monitor, grade and assist. Group simulations can also be done, allowing multiple students and/or instructors to view and perform in concert. These simulations can also be used for examination of students in order to determine suitability for practice in the field.

Often in practice, surgeons do not use the most up-to-date methods. Surgical knowledge is typically passed on through schooling and residency. When a surgeon is taught how to perform a particular procedure, they will learn the method used by the instructor. The instructor in turn will be teaching the method they are most familiar with, which may not be a current method. Using augmented or virtual reality as a training mechanism, practitioners can be kept up to date with the latest techniques in performing procedures. Through interactive simulations, a surgeon can train in the most current methods of performing a particular procedure. Software can also be updated regularly to ensure that the most up-to-date methods are available for training, reducing morbidity and mortality in patients.

Another embodiment relates to a method and apparatus for teaching and testing using artificial intelligence coupled with virtual and/or augmented reality.

Using virtual space to visually present materials to a student, artificial intelligence algorithms can be applied in order to test whether the material has been learned by the user, and to adjust the rate and style of teaching to match the needs and preferences of the user.

Another embodiment relates to a method and apparatus for first aid training using augmented reality, virtual reality, or another virtual space.

First aid training is a common form of medical training available to a large portion of the population. Traditional first aid training, however, doesn't allow the user or users to experience real situations in which first aid could be necessary. By using a virtual space, first aid situations can be simulated, and the user(s) can be given guidance and training in the necessary steps to perform the required aid. The simulation can also be used to evaluate the performance of the user(s) and determine whether they should be deemed competent in taking action in a first aid situation.

Another embodiment includes a method and apparatus for intelligence quotient (IQ) testing using augmented reality, virtual reality, or other virtual space.

IQ testing is done using a variety of tests involving different aspects of intelligence. These tests can be administered in virtual space, and the results evaluated automatically, or with any degree of evaluator interaction. Normally an examiner monitors the subject during the test to evaluate performance. This is frequently a cause of anxiety for the subject being tested, which can lead to less than optimal performance. Using a virtual space test removes the need for an examiner to monitor the subject.

Another embodiment is a method for teaching students using augmented or virtual reality combined with artificial intelligence.

Another embodiment is a game in which the user or users are instructed which simulated organ to remove from a virtual patient. If the user successfully removes the organ, they receive a point. If they do not, they are rewarded with a sound or other feedback mechanism. Turns are taken by multiple users to reach the highest score and determine a winner.

Another embodiment relates to a method for providing an augmented or virtual reality anatomical display, comprised of elements including, but not limited to, anatomical diagramming and labelling, veterinary anatomy, and dissection simulations.

Anatomical display can be done in augmented or virtual reality using pre-created and optionally annotated models. These models are displayed in three dimensions, and can be interacted with by the user or users. By using voice, gesture and other user controls, the user or users can manipulate individual parts of the body. The user(s) can also specify which layers and portions of the anatomy to be displayed. Individual parts, for example organs, can be separated from the main model for closer inspection and to provide greater detail about the selected feature.

Figure 10:
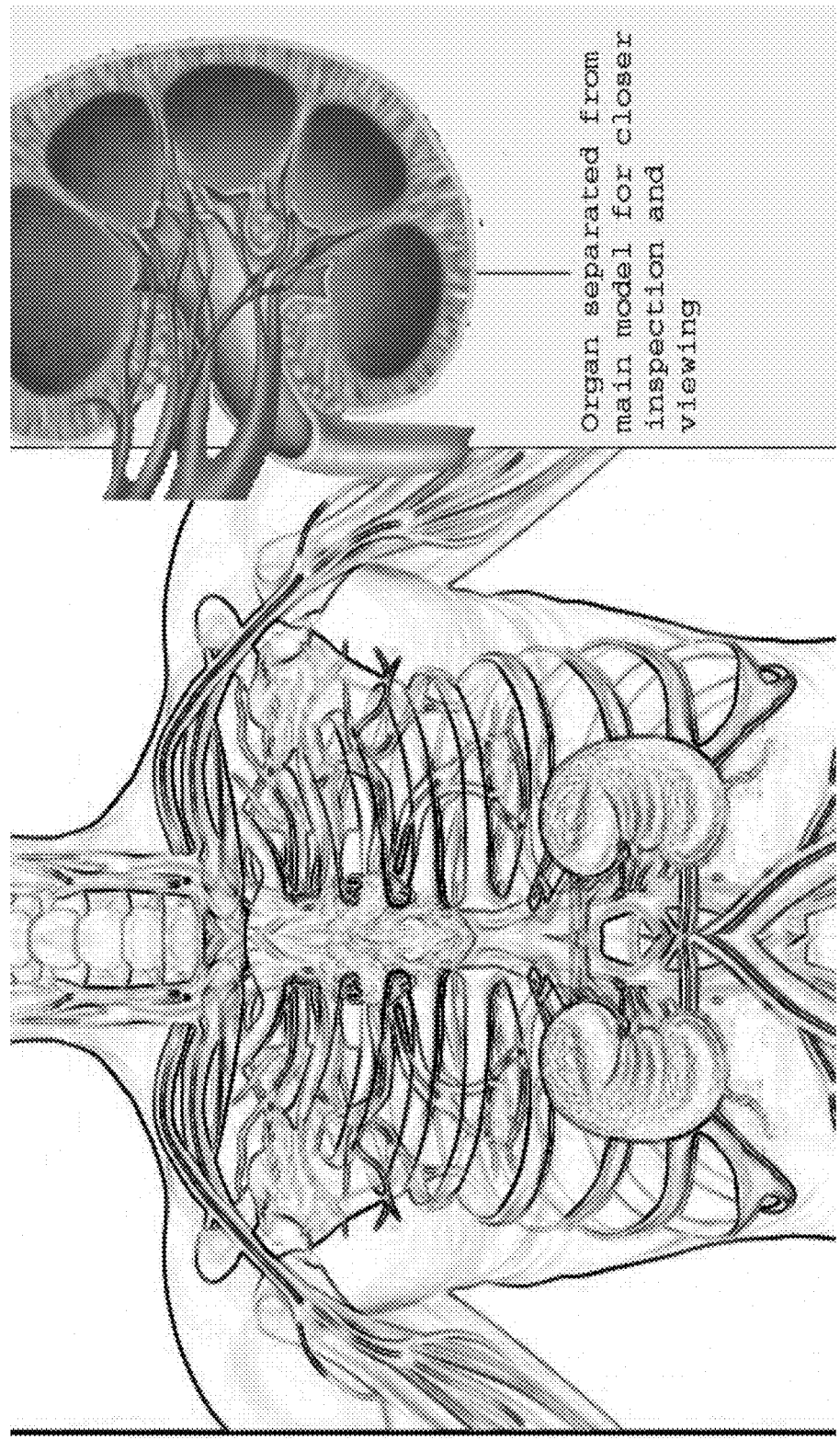
FIG. 10 illustrates an exemplary patient anatomy display with an element of the anatomy virtually removed to permit visibility to otherwise obstructed portions of the anatomy.

FIG. 10 shows an augmented reality anatomical model with a kidney removed for closer inspection. The kidney has been modified to display a cross section.

These diagrams can be of humans, animals or any living organism. Simulations can also be prepared for dissection, allowing a student to interact using a controller, gestures, or other means of user interface in order to attempt to perform a dissection, with feedback given to tell the user if they've made a mistake.

Figure 11:
FIG. 11 illustrates an exemplary active dissection [using system component?]

FIG. 11 shows a user dissecting a virtual cadaver, removing a section of the epidermis to reveal the tissue underneath.

For example, in a classroom environment, this cuts out the need for gross anatomy, which has fallen out of favour due to health regulations. Instructors and students can explore anatomy in a virtual body, rather than having to deal with the costs and regulatory issues surrounding the use of cadavers, and in a more hands-on fashion than that afforded by traditional textbook based learning. Another advantage is the ability to reverse steps, which would obviously not be possible in the case of a cadaver.

In another example, during examination of a horse, an augmented reality display of equine anatomy can be displayed in the veterinarian's HUD, giving quick access to anatomical data and improving efficacy of examination and treatment.

Another embodiment relates to a method for combining gross anatomy with problem based learning (PBL).

Gross anatomy is the study of anatomy through the use of cadavers or other anatomical teaching methodologies, while PBL is a pedagogy in which students learn about a subject through open-ended problems. The two methods can be combined in order to create a learning paradigm in which open-ended problems are combined with anatomical dissection in order to teach a more thorough understanding.

For example, an instructor could pose a problem involving a patient who has passed away. In the hours prior to death, the patient repeated the same question over and over, despite receiving an answer to the question each time. Students can then use a virtual body for dissection to determine the cause of death, in this case an insulin-secreting tumour of the pancreas.

Another embodiment relates to a method for providing an augmented or virtual reality medical simulation, comprised of elements including, but not limited to, diagnostic simulations, surgical simulations, procedural simulations, previewing surgeries based on patient imaging, and group simulations for purposes such as teaching.

Medical simulations are useful for training and testing practitioners without risk to patients. Using data acquired from a real patient, or constructed using a 3d modelling program or through other computer generated means, a patient is created in virtual space.

A virtual patient can have a condition as selected either automatically by the software, or with user interaction for example by an instructor. The user or users can interact with the virtual patient in order to diagnose the condition. Virtual diagnostic tests can be run on the patient, giving results accurate to the condition the patient is displaying.

Figure 12:
FIG. 12 illustrates an example of a virtual patient having an evident symptom (e.g., a rash or other topical ailment)

FIG. 12 shows a virtual patient with a visible rash. The patient is to be examined and diagnosed by the user.

A user can also perform a surgery or procedure, either as part of a simulation involving a diagnosis or separately. The virtual patient responds as would a real patient, and complications can optionally be introduced either automatically or interactively.

Surgical previews can also be performed using imaging data from real patients. These images are transformed into a model usable by the simulation, and a surgical procedure is simulated using the anatomy of an actual patient.

For example, a simulation could begin with a virtual patient in a doctors office. The user must question the virtual patient and determine the appropriate diagnostic tests for a diagnosis. In this example, the patient has pain in the lower back due to kidney stones. In order to diagnose this, the physician orders an abdominal MRI. In the simulation, the results of the test are made available immediately. Using the MRI, the user correctly diagnoses the kidney stones and is able to schedule the patient for surgery. The simulation then moves to a surgical environment, and the user is able to perform the simulated surgery to treat the patient.

In another example, a practitioner taking an examination can be subjected to a demonstrative examination of skills. Surgeons, for example, are certified by taking a written and not a demonstrative exam. By performing a procedure in virtual reality, the ability of a candidate can be evaluated in a realistic scenario. The procedure is monitored by an instructor or other qualified individual who then grades the candidate and determines whether they are qualified to carry out the skills being examined. Alternatively, criteria can be established for varying degrees of success or failure, to be evaluated by the program of the simulation and presented to the candidate and/or instructor.

In another example, a surgeon preparing to install a pacemaker in a patient reviews the patient's radiological data in virtual reality. A model of the patient is constructed and placed on a virtual surgical table. The surgeon is able to use virtual surgical tools to install the pacemaker in the patient, using the real patient radiological data, in advance of performing the actual surgery. This allows the surgeon to prepare for any abnormalities in the patient physiology as well as practice the procedure for efficacy.

Another embodiment is a means of creating three dimensionally printed cadaver models for anatomical use, surgical practice and other means. Using three dimensional models created using the explained method from radiological data, a model suitable for three dimensional printing is generated. This model is of sufficient detail and accuracy to be used in place of a cadaver for purposes of anatomical study, surgical practice and other common uses. This also allows for printing of defective organs prior to surgical repair which can be used for practice and study of techniques. This also allows for problem based learning combined with gross anatomy in both real and virtual settings.

Three dimensional models of animals and other organisms can also be created, allowing for veterinary and other disciplines to perform dissection and anatomical study on species which are either uncommon or otherwise difficult to study. An additional benefit of this method is that the subject does not actually need to be killed. This is particularly useful with endangered species, where a dissection is not possible, but collection of radiographical imaging may be possible.

For example, radiological data from patients with tumors are used to create three dimensional cadaver models for a classroom. Each cadaver is then associated with a set of symptoms and radiological reports. Students must then correctly identify the issue, and perform the surgical procedure on the cadaver to remove the tumour.

In another example, a man dies of unknown causes. The family does not wish an autopsy performed, however the police have questions regarding the mans death. By scanning the body in an MRI, a three dimensional cadaver model can be created, which can then be autopsied without violating the family's wishes.

Another embodiment relates to a method of using augmented or virtual reality combined with artificial intelligence for the purpose of testing and teaching materials to students.

Students learn in many different ways. Using artificial intelligence and virtual space, pre-programmed material can be presented to a student in an engaging fashion. By continuously testing the students knowledge of the subject material, the methods which are most effective for the particular student can be determined, and teaching can be accelerated.

Figure 13:
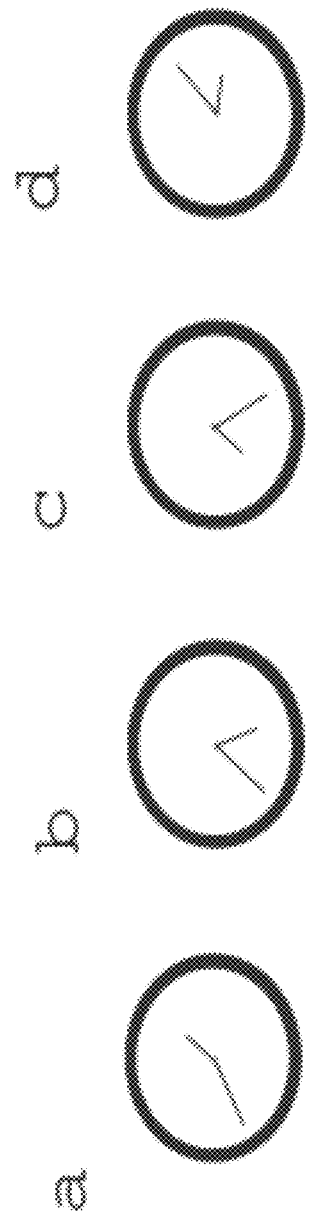
FIG. 13 illustrates an example of student learning in augmented reality.

FIG. 13 shows a multiple choice question displayed in augmented reality for a student.

The virtual space can also be used for testing of the pre-programmed material. A student is asked to respond to questions, or to perform tasks, or otherwise interact with the virtual space as defined in the program. Based on the success or failure of the responses, a grade can be assigned and areas of improvement can be identified.

For example, a child with a learning disorder is introduced to a virtual or augmented reality learning environment. Information about dogs, cats and fish are presented in different fashions. Dogs are taught using visual cues. Cats are taught using audio methods. Fish are taught using an interactive display which can be touched and manipulated. The child is then tested to determine which portions of the material were learned best. This is repeated over multiple topics, both to improve accuracy and to account for cases in which the child has foreknowledge of the subject area, and a learning profile is created and adapted for the specific child. New material is then presented using the adapted methodology, and testing is used to continuously update the learning model.

In another example, dyslexia can be diagnosed using a series of words designed to test pronunciation and reading. Each word is presented in augmented or virtual reality, and the user is asked to read the word out loud. Speech recognition is used to determine whether the word has been repeated correctly. Based on the number of words repeated correctly, an assessment can be made as to whether additional screening for dyslexia is required. The test can also be monitored remotely by another user with a different device. This allows for testing without the subject being anxious about being monitored during the test, helping them to perform better.

In another example, a student is given a test consisting of twenty-one questions. Seven questions are given to the student verbally. Seven questions are given to the student visually. Seven of the questions require the student to interact with virtual objects. The results of the test are analyzed both for an overall grade, and for grades in each individual learning type. A profile for the student is built, determining if the student scores higher on questions posed in a particular style. When a preferred style is determined, material will be presented more often in the preferred format to assist the student in learning.

In another example, a child with a learning disorder is introduced to a virtual or augmented reality learning environment. Information about dogs, cats and fish are presented in different fashions. Dogs are taught using visual cues. Cats are taught using audio methods. Fish are taught using an interactive display which can be touched and manipulated. The child is then tested to determine which portions of the material were learned best. This is repeated over multiple topics, both to improve accuracy and to account for cases in which the child has foreknowledge of the subject area, and a learning profile is created and adapted for the specific child. New material is then presented using the adapted methodology, and testing is used to continuously update the learning model.

Another embodiment is a means of performing a hearing test using an augmented or virtual reality device. The test is performed by first instructing the user to indicate when they hear a sound. Sounds are then played in increments, starting at a frequency well below normal human hearing range, until the user indicates they can hear the sound. Once the sound is heard, the increment is reduced and the frequency is reduced until a sound is played and the user does not indicate hearing it. This is repeated until the lowest frequency heard by the user is found. The user is then tested in the high frequency range, beginning at a frequency well above normal human hearing range. The frequency is decremented until the user indicates that they can hear the sound. The increment is then reduced, and the frequency is increased until the user no longer hears the sound. This is repeated until the highest frequency heard by the user is found.

For example, a child who is thought to be deaf is exposed to a virtual environment and connected to vitals monitoring. The child is then exposed to various sounds, and the vital signs monitored. A response by the child to the sounds indicates that they are able to hear the sounds, and can be used to assist in diagnosis of conditions such as non-verbal autism.

In another example, an aging woman is thought to perhaps be hard of hearing. By having her perform the test, her auditory range can be verified and it can be determined whether she has a need for a hearing device.

Another embodiment relates to a method for augmented or virtual reality simulation for the purpose of training a user or users in first aid.

First aid training can be done in a virtual space using pre-programmed simulations. A user interacts with three dimensional models in a virtual space, following instructions given either by the computer running the simulation, or by a live instructor. The instructor, and other users, can optionally view the virtual space at the same time as the training user. Feedback is provided by the simulation. The simulation can also be used for testing and grading of users.

Figure 14:
FIG. 14 illustrates an example of a first-aid procedure.

FIG. 14 shows an augmented reality demonstration of a patient receiving a tourniquet. The demonstration is given by a virtual instructor, following which the user is invited to repeat the procedure.

For example, a group of students is learning to apply a tourniquet in a first aid situation. A virtual reality program, complete with virtual instructor, gives the group a demonstration of how the tourniquet is tied. After the demonstration has been completed, each student is able to attempt a tourniquet on their own virtual patient. When a student is having trouble, they can request assistance from the program. When students complete their tourniquet, the program evaluates their level of competency and assigns a grade towards their first aid course.

Another embodiment relates to a method for doing intelligence quotient testing using augmented or virtual reality.

IQ testing is frequently done in the presence of an examiner, which can make some subjects nervous and affect performance. By administering the test in a virtual space, the user can take the test free of the distraction of being watched. The administrator of the test could optionally watch the process in virtual space without being visible to the user.

The test is administered using the same test questions that would be used in a written/physical test, however all material is asked and answered in a virtual space. This also allows for more advanced testing in areas such as spatial reasoning.

Figure 15:
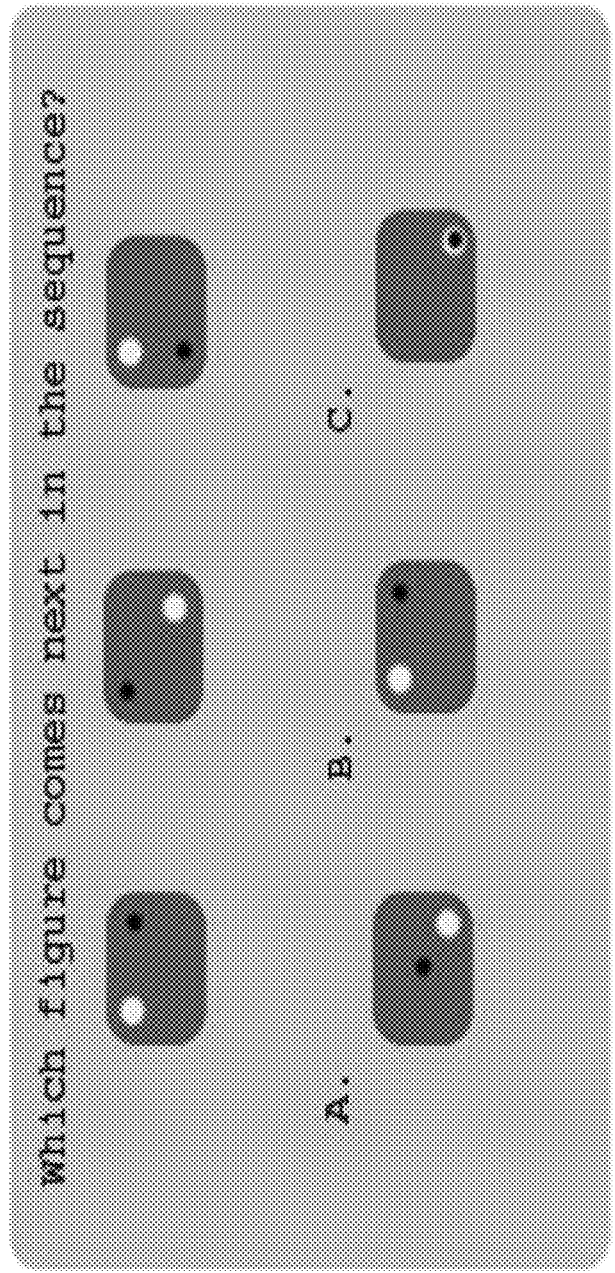
FIG. 15 illustrates an exemplary IQ-test question presented in augmented reality.

FIG. 15 shows a question posed for an IQ test in augmented reality.

For example, a test for spatial reasoning may involve a question of which of a series of shapes will correctly fill a three dimensional hole. In augmented reality, the user is able to examine the shapes in three dimensions, manipulating their orientation and size. This allows the user to better analyze the possible solutions to the problem before making their selection.

Another embodiment relates to a method for teaching students using augmented or virtual reality combined with artificial intelligence.

By combining augmented or virtual reality and artificial intelligence, an enhanced learning system can be created for teaching of subject matter. Different people learn in different ways, with aural, tactile and visual being the three primary methods. By using artificial intelligence and a databank of information to be taught, the optimal learning style of a student can be gauged and utilized to ensure better understanding of the teaching material.

By periodically assessing the student, the areas which the student has not fully learned the material can be determined, and additional teaching and focus can be provided on those areas. Using a combination of teaching using different balances of the aforementioned methods, the students' best learning styles can be established either in whole or in different areas, and by adapting the teaching methods to the student, learning and retention are enhanced.

For example, a student who learns very well from written instruction is being taught how to perform a science experiment. Different parts of the experimental method are imparted to the student using different teaching methods: aural, tactile and visual. The program notes that the student is best able to follow the instructions when they are presented visually, and therefore begins to present a higher proportion of the instructions in a visual manner.

III. Physiological/Anatomical Mapping, Modeling and Positional Marking

Another embodiment relates to a method and apparatus for scanning, mapping and analyzing human bodies.

Using a camera or other visual recording device, a subject can be scanned and mapped into a two or three dimensional model. This model can be used by a practitioner to identify areas of interest or concern. The model can also be used to monitor areas between visits. The model can also be analyzed, automatically or with user-interaction to determine the presence of conditions such as melanoma, rashes, psoriasis and other visible conditions.

In the case of a two dimensional mapping, a camera is directed at the subject. The subject then turns 360 degrees and images are recorded as the subject turns. The recorded images are first processed to remove the background by comparing identical data from one frame to the next. Identical data is discarded, leaving only the subject. Using feature detection, the images are then stitched together to form a two dimensional model of the subject.

In the case of a three dimensional mapping, a camera is directed at the subject. The subject then turns 360 degrees and images are recorded as the subject turns. The recorded images are first processed to remove the background by comparing identical data from one frame to the next. Identical data is discarded, leaving only the subject. A two dimensional model is created as explained above. A point cloud is then generated from the data, creating a three dimensional model of the subject. The point cloud is then overlaid with the two dimensional model ("skin") which gives a three dimensional model of the subject.

Once the model has been created, analysis of the two dimensional model ("skin") is performed for known conditions. Areas of interest are marked for review by the user or users. The data is also stored for comparison upon future visits.

Another embodiment relates to a method and apparatus for timing the pulse sequences of magnetic resonance imaging based on the position of the subjects' body in order to ensure that images are taken at the same point in a rhythmic movement such as breathing or a beating heart.

Magnetic resonance imaging (MM) with a traditional Mill machine is subject to imaging problems related to patient movement. Blurred images and image artifacts are two common issues seen when a patient moves during an Mill exam. By monitoring the position of the patients body, the imaging sequence can be timed such that an image is taken only when the patient is in the correct position.

For example, a sensor or camera can be used to monitor the height of a patients chest, triggering the imaging sequence to take an image only when the chest is at the same height as the last image. Using this technique, all images of a patients chest would be taken when the chest is in the same position.

Another embodiment relates to a method for enhancing positional location in augmented reality using gadolinium markers.

Another embodiment relates to a method and apparatus for controlling the visualization of a three dimensional object in virtual reality, augmented reality, or other virtual space.

A three dimensional object stored in a computer consists of many data points. By altering the visualization, the visual representation of the object can be changed allowing a user or users to view the visualized object in different ways.

For example, a three dimensional model created from Mill data contains a great deal of information that is covered by the outer layers of the model. By altering the visualization and removing the outer layers of data, the inner portions of the model (such as the brain) can be made visible.

Another embodiment relates to a method and apparatus for visualizing medical imaging data in augmented reality, virtual reality, or other virtual space.

Medical imaging data can be converted to a format suitable for display in three dimensional virtual space. This data can then be displayed through virtual reality, augmented reality, or another virtual space.

Positional location in augmented reality is determined primarily through visual means, feature detection, and other methods described herein.

Another embodiment relates to a method and apparatus for constructing a three dimensional model comprising the steps of determining image separation distance, identifying missing images, aligning source image and constructing missing image data, and merging the images to form a three dimensional model.

Another embodiment includes a method for mapping and analyzing human bodies, comprised of scanning of the body, storing of surface data, marking of important features such as melanoma, moles, rashes, other skin conditions and remarkable features (either automatically or by human interaction).

A subject or subject area can be scanned using a camera or other imaging device. The surface data can then be stored and analyzed for current and future use. By analyzing the characteristics of the surface, common conditions can be diagnosed, and efficacy of treatments can be determined. Sizes, colour and other metrics of an affected area can be measured and compared, allowing a direct comparison between previous visits and current visits. This comparison also gives a clear view of the efficacy of treatments being provided. These comparisons can be used by, but are not limited to, the practitioner as well as, for example, an insurance company to determine whether they're willing to continue reimbursing the patient for a given treatment.

For example, a visual recording of a patient is taken with augmented reality glasses is stored, complete with a visual overlay of diagnoses made either automatically or with user-interaction. This recording can then be used as a visual report for the patient file, and for review prior to appointments with the patient. The recording can also be used as part of a referral to a specialist (including all AR/VR content). The recording can also be used as part of a referral to a specialist. In a hospital setting, the visual record can be used to prevent the need to re-examine a patient at different stages of their treatment. A recording of the original exam can therefore be viewed.

In another example, a patient with eczema could be scanned at an initial consultation. As the dermatologist treats the eczema using a prescription, the scan can be compared at each visit to verify the efficacy of the treatment. Software can automatically determine whether the size and shape of the affected area has changed.

Another embodiment relates to a method for timing imaging sequences based on position of the patients body, for example using the height of the chest to ensure that images are taken at the same point during the breathing process to give a more stable image.

In traditional imaging sequences, movement of the patient can cause failed imaging sequences, artifacts, blurred images, and/or other undesirable anomalies. By using a sensor, for example a camera, altimeter, or other positional sensor, the imaging sequence can be timed to take images only when the patient is in the correct position.

For example, in doing an MR scan on a patients chest, a camera can be used to monitor the height of the patients chest from the MR platform. When the patients chest is at a specific height, the imaging sequence is fired. When the patients chest is no longer at the correct height, the sequence is paused awaiting the next time that the chest position is correct.

Figure 16:
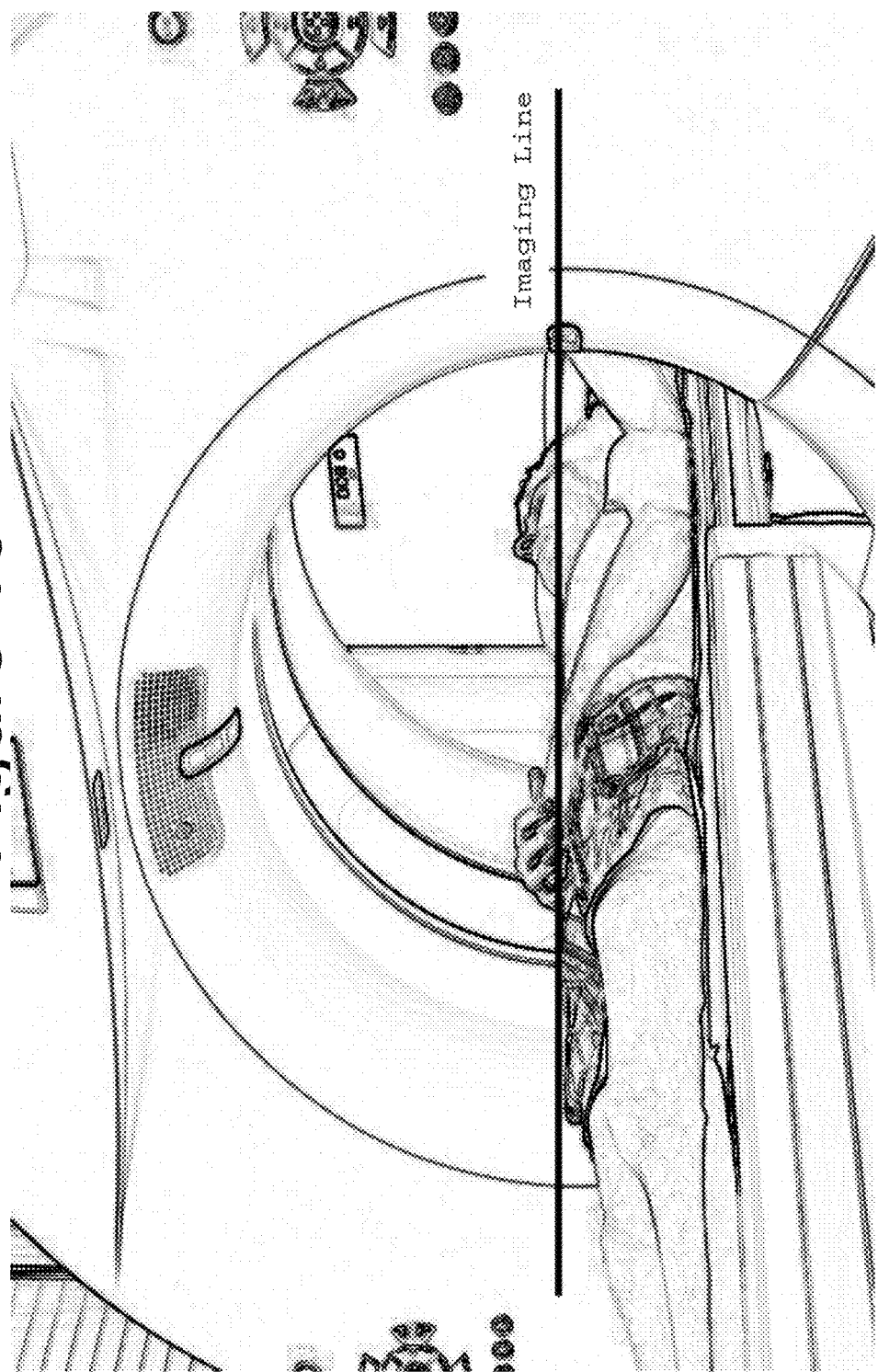
FIG. 16 illustrates an exemplary chest rise and detection/image capture thereof.

FIG. 16 shows a patient in an MRI machine. An imaging line is shown in the image, which is a line tracked by a camera or other imaging device at which images are taken. When the patient's chest is not level with the line, imaging is not taken.

Another embodiment includes a method for controlling the visualization of a three dimensional object displayed in virtual reality, augmented reality, or other virtual space comprising the steps of determining the requisite change in visualization, and updating the three dimensional object. An apparatus for controlling the visualization of a three dimensional object displayed in virtual reality, augmented reality, or other virtual space comprising a means of determining the requisite change in visualization, and a means for updating the three dimensional object. The process may be performed automatically by a system or may be guided interactively by an operator. Applications include, but are not limited to, virtual reality, augmented reality and three dimensional printing.

A visualization in virtual space can be controlled in a variety of different ways under the invention. In one embodiment of the invention, the model display depth is controlled automatically or by user interaction to display parts of the model not initially visible. The model can either be densely packed (including all information) or a "hollow" model consisting of perimeter information only to a limited depth. This perimeter information can be calculated using negative space exploration. As the user indicates a portion of the model they would like to see deeper, the outer sections of the model are hidden and the underlying data is displayed.

Negative space exploration is done by selecting an empty starting point at the edge of the model's Cartesian space, frequently at (0, 0, 0) [x, y, z coordinate]. Each adjacent coordinate is added to an exploration list provided that the coordinate does not satisfy the search parameter, for example a minimum colour value threshold. When a point is met which satisfied the search parameter, it is added to the object's perimeter array, and in the case of depths greater than one coordinate the depth counter for the angle is decremented. Coordinates satisfying the search parameter are not added to the search list.

Figure 17:
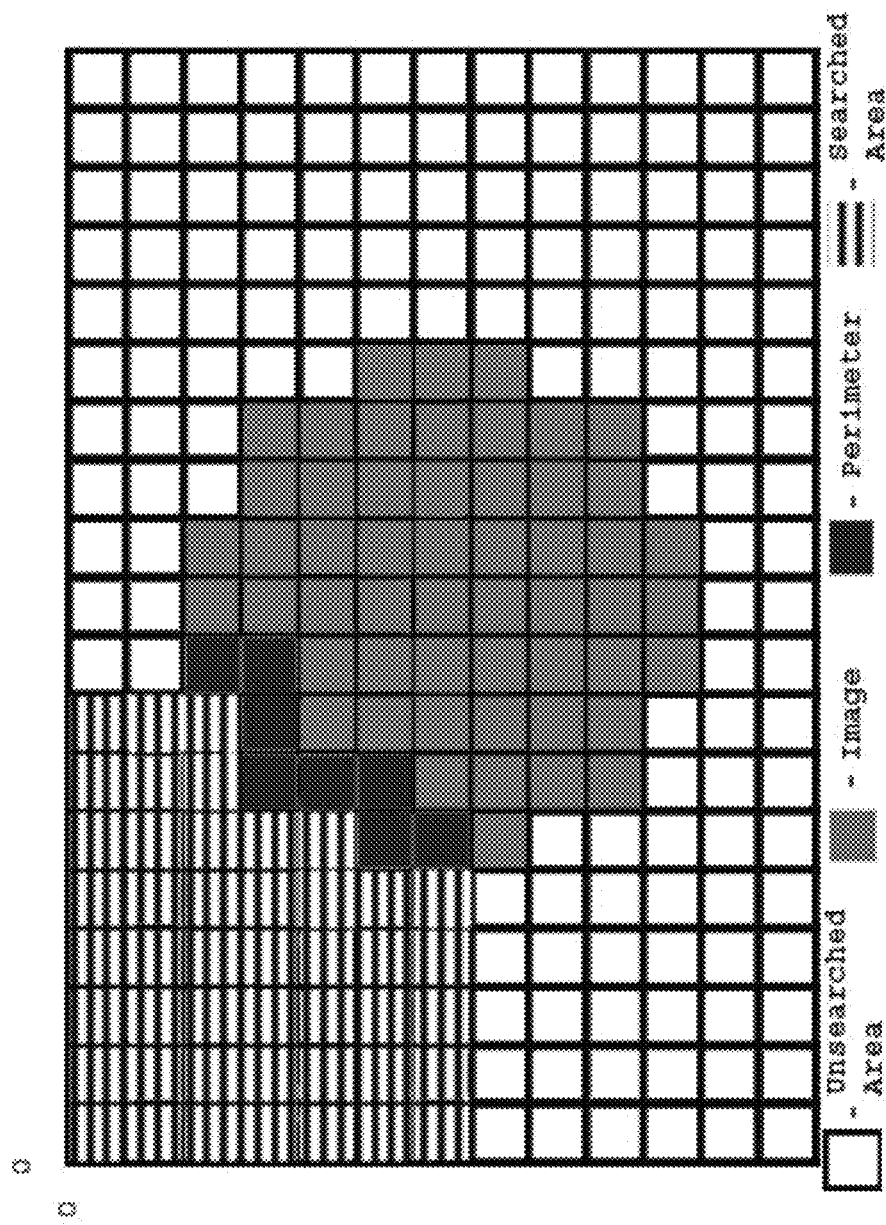
FIG. 17 illustrates an example of negative space exploration.

FIG. 17 shows an example of two-dimensional negative space exploration. The exploration started from the point (0, 0) in the top left corner. Points were added to the searched area (see legend) and adjacent points tested for non-zero (white) values. Along the top left perimeter of the circle (Image, see legend) non-zero points have been found (Perimeter, see legend). These points satisfy the non-zero search parameter and are added to the perimeter array. Therefore, as of the point in time depicted in this figure, the perimeter array contains the points: (8, 3), (8, 4), (7, 4), (6, 4), (6, 5), (6, 6), (5, 6), and (5, 7).

In the case of updating a hollow model, data from the complete model is used to determine the data to be displayed at the new depth location. For example, if the initial depth along the x-plane is 0, and the user has updated the depth to be 10, all coordinates in the existing model with an x-value less than 10 are discarded from the model. Data from the complete model is then added along the x=10 plane of the model. Additionally, data to a given depth can be added. For example, if the depth to be used for the model is 3, data in the range 10<=x<=13 would be added to the visible model.

Another embodiment includes a method for visualizing medical imaging data in augmented reality, virtual reality, or other virtual environment, comprising the steps of locating the subject, determining subject position, determining subject orientation, and rendering the medical imaging data. An apparatus for visualizing medical imaging data in augmented reality, virtual reality, or other virtual environment, comprising a means for locating the subject, a means for determining subject position, a means for determining subject orientation, and a means for rendering the medical imaging data. The process may be performed automatically by a system or may be guided interactively by an operator. Applications include, but are not limited to, visualization for the purpose of surgical procedures, visualization for the purpose of medical testing, visualization for the purpose of surgical training, visualization for the purpose of medical training, visualization for the purpose of physiotherapy, visualization for the purpose of laser surgery, and visualization for the purpose of physical diagnostics.

Locating a subject can be done in a variety of different ways. In one embodiment of the invention, features in the subject area are compared to features detected in the target. If the number of matching features is greater than a threshold, determined either automatically or through user or program specification, then the target is deemed a match to the subject and the match location is found. In another embodiment, the perimeter shape of the target can be compared to detected edges in the image. If the number of matching perimeter points exceeds a threshold, either automatically determined or specified by a user or program, then the target is deemed a match to the subject and the match location is found. This process can be applied in three dimensions using, for example, a pre-compiled set of features or perimeter data for different angles and scales of the target. Additionally, the rotation and scale of the target can be determined in real-time during feature or perimeter comparison.

Figure 18:
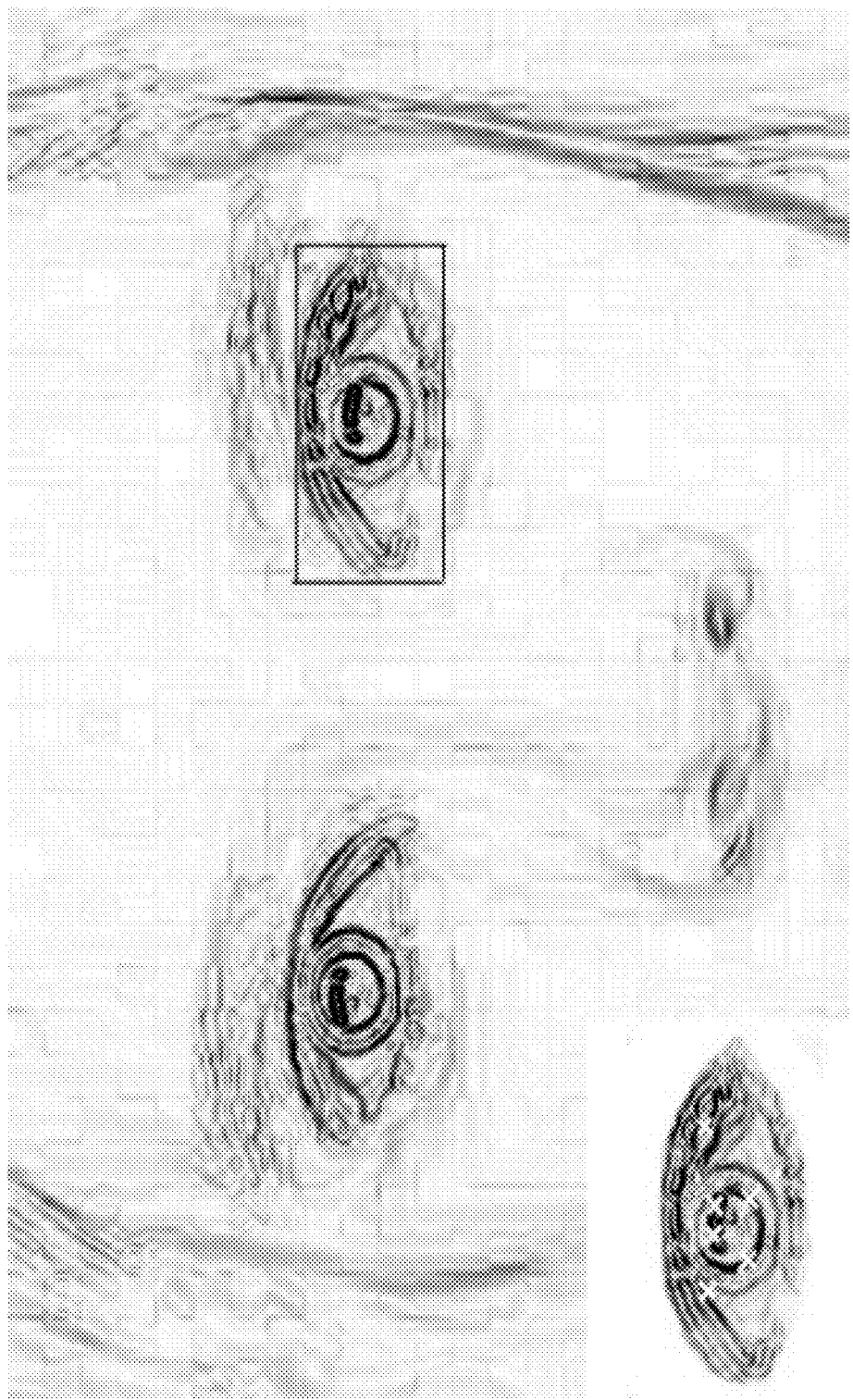
FIG. 18 illustrates an example of sequence matching based on features and/or perimeter.

FIG. 18 shows a target object (bottom left corner, white background) being located and matched in an image. The white X marks on the target object indicate features. These features are matched to features in the subject image to find a positive identification. The perimeter values of the target object are also compared to the subject image to find and/or reinforce the match. The matching area is shown with a black square surrounding it.

The search area within the subject can be further reduced in order to make detection of targets a faster process. One embodiment of the invention uses an XOR (exclusive or) method to determine points in the image which have changed, indicating movement of objects within the subject. These motion points are used to guide the search for targets in the subject, reducing the number of data points that need to be examined. These points can optionally be used as replacements for features and/or perimeter data.

In order to determine the XOR based image, the offset between frames is required. To determine the offset between frames, the current subject image is compared to the previously seen subject image. A number of points (n) is selected either automatically, by a user, or as a part of the program. These points are fixed locations in the view frame. By comparing the data in the previous image to the data in the current image, an offset can be determined. One point is selected as a starting point. An area, either predetermined, automatically determined, or selected by a user, is searched for a match to the value of the previous image. The value to be compared can be, for example, a single point value. The value can also be the summation of a Gaussian distribution or other means of calculation. If the value in the current image is found to match the value of the previous image within the given range, then the offset is recorded. Other possible offsets within the range are also recorded. If no possible offsets are found, then another point is selected until either a match is found, or a subsequent match for the offset (see below) is no longer possible.

Figure 19:
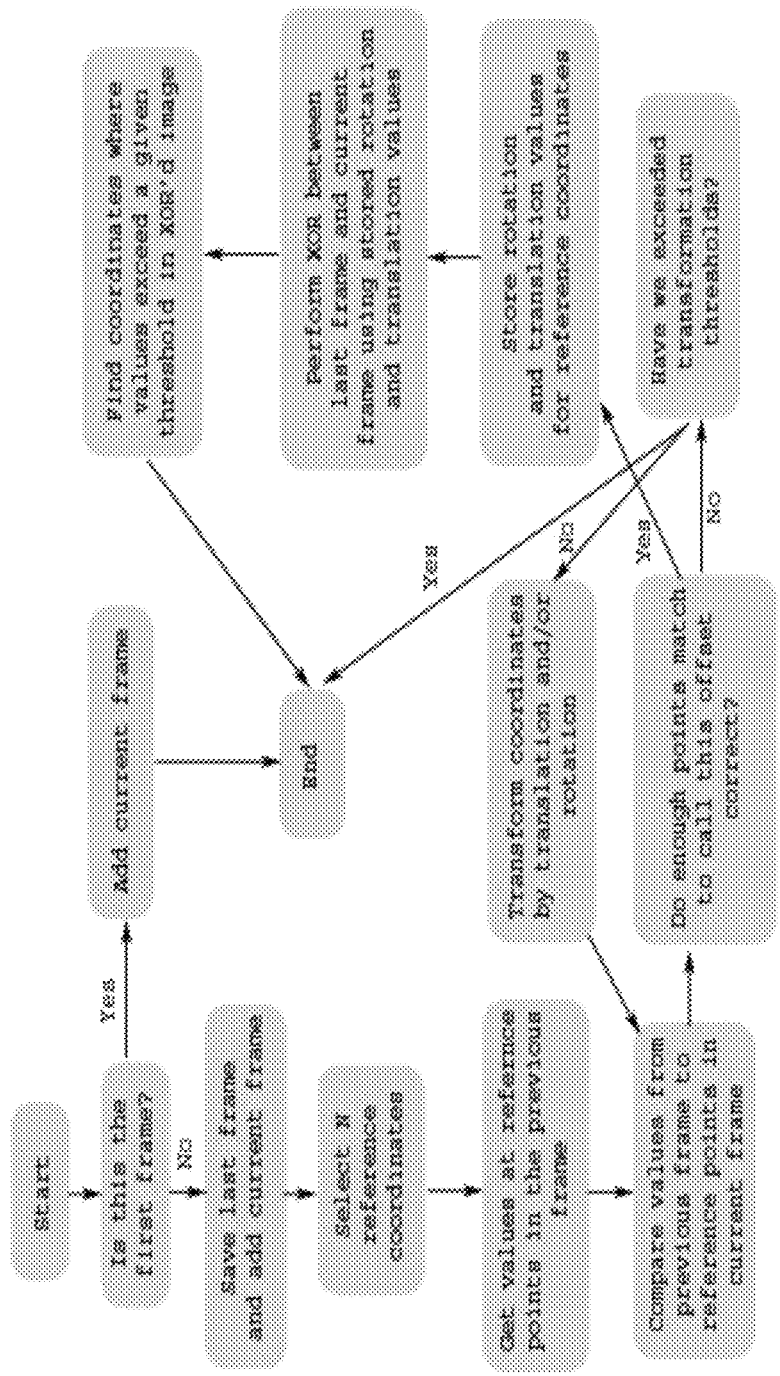
FIG. 19 illustrates an exemplary frame-offset system.

FIG. 19 shows a flow chart for frame offset calculation. The flow begins at Start in the top left corner. If this is the first frame of the sequence (e.g. First image captured from a camera), we simply save the current frame and complete the sequence. If this is any subsequent frame, we store the previous frame and add the current frame. Next, a number of reference points (N) are selected, either at predefined coordinates or by some other means of selection. These reference coordinates are used to retrieve values from the previous frame. The values are stored for later use. The values at the reference coordinates in the current frame are then compared to those taken from the previous frame. If a sufficiently high number of values do not match, then a transformation of coordinates will occur. First, the transformation values are tested to ensure they haven't exceeded thresholds. If they have, the sequence is aborted and no match is found. If they have not, then the translation and/or rotation values are adjusted in a logical fashion to test values within the threshold ranges. The cycle of comparison and adjustment is continued until either the transformation threshold is exceeded and the sequence ends without a match, or a sufficiently high number of values do match and the rotation and translation values are recorded. Using the recorded translation and rotation values, the previous frame and current frame are then combined using an XOR operation, giving a new frame of the same size as the original frames. By finding coordinates within the XOR'd frame which exceed a given threshold, the locations of objects and other moving components of the image become visible.

Once the list of possible points is completed, each of the remaining n points is compared at the same offset. These points are also rotated based on the center of the image and tested. If enough of the points match at the specified offset and rotation, a match is determined to be found. At this point, all of the pixel values in the target image are XOR'd with the subject image, modified by the determined offset and rotation. Points which do not exceed a threshold (either determined by a user, automatically, or predetermined) are removed. This composite image highlights the locations of objects and movements within the subject area.

A feature is determined to exist if a sufficient number of sequential points on a circle at a fixed distance meet a minimum threshold criteria. For example, if the minimum number of sequential points is determined to be 16 and the match requirement is a value greater than 10, then a minimum of 16 points in a row on the circle (calculated based on a variable or fixed distance) must have values greater than 10. If this condition is satisfied, then the center point of the test is deemed to be a feature.

Figure 20:
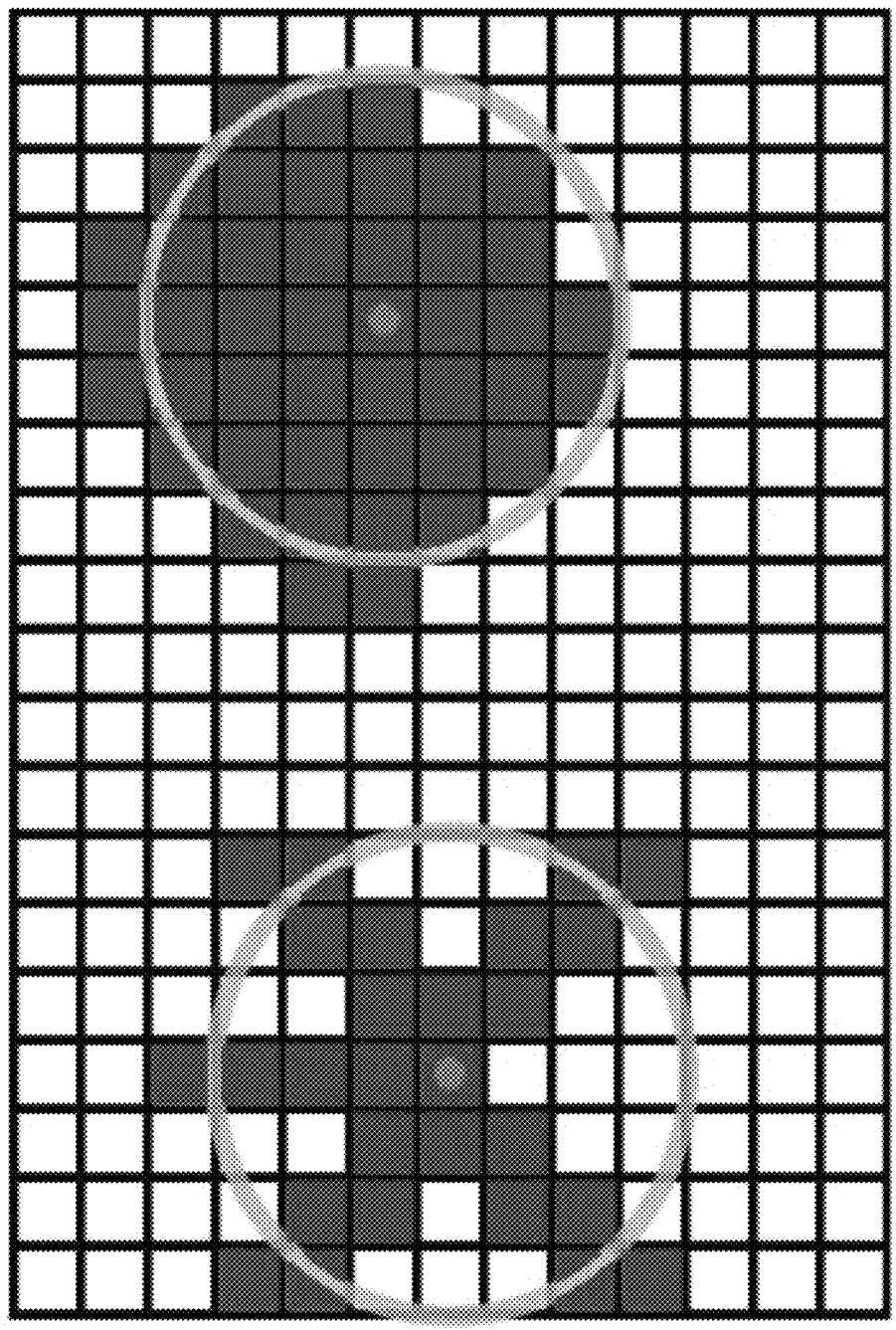
FIG. 20 illustrates an exemplary circular test for two-dimensional features.

FIG. 20 shows feature tests performed in two dimensions on two different points. Using a minimum number of sequential points of 12, the point on the left (center of the left circle) does not pass. There are fewer than 12 points sequentially on the circle which contain a non-white point. The point on the right (center of the right circle) does pass. There are 13 points which are sequentially on the circle surrounding the point.

Feature matching can be done in three dimensions using either planes or a sphere. In the case of a plane, the circle as noted above is calculated on three different planes. The X-Y plane, the X-Z plane and the Y-Z plane. If the feature meets the criteria for all planes, then a match is determined to exist.

Figure 21:
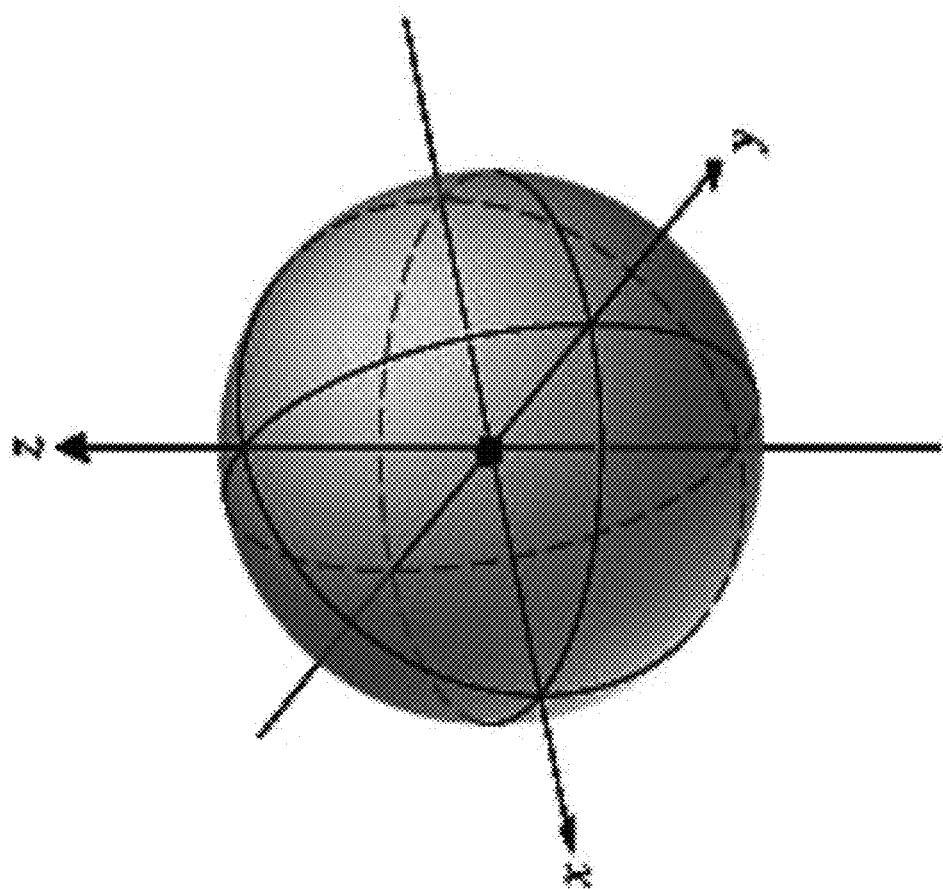
FIG. 21 illustrates an exemplary spherical test for three-dimensional features.

FIG. 21 shows a three dimensional model of the feature test. The planar circles shown as rings around the outside of the circle represent the circle used on each axis to determine whether the feature is valid. A test is done in each plane—XY, XZ and YZ—and if the feature test is successful in all three planes, then a feature at the center—the black dot at the origin in the figure—is determined to be valid.

The location of the target is stored as both 2D coordinate data for immediate viewing, and 3D coordinate data for reference to movement. Using the matched rotation and scale of the target, the target can be accurately rendered over the matched area in the subjects view. By storing the location in three dimensions, the object can quickly be tested in subsequent frames to confirm its location as the user and target move.

Another embodiment relates to a method for enhancing positional location in augmented reality using gadolinium markers.

Gadolinium is a material commonly used to enhance contrast in MR imaging. By mixing gadolinium with a carrier, a surface can be coated prior to an MR scan. This gives a high contrast image of the coated surface suitable for use in target detection for virtual spaces.

For example, a patient is having an MR scan to look for lesions in the brain. The gadolinium infused carrier is spread across the patients face prior to the MR scan, which creates strong contrast in the patients face. The enhanced contrast from the patients face is used to create a digital image of the patient, allowing facial recognition to be used to identify the patient and position a three-dimensional model of the MR scan over the patients head during a later surgery.

In another example, the gadolinium infused carrier is used as a marker drawn on the subject, which is visible in the final MR image and can be used for calibration.

Another embodiment is a method of constructing a three dimensional model comprising the steps of determining image separation distance, identifying missing images, aligning source image and constructing missing image data, and merging the images to form a three dimensional model.

Images provided in DICOM format contain data indicating the separation distance between slices. This data is used to determine the number of slices required. Absent this data, the lesser of the width and height dimensions of the image are used to determine depth, creating a rectangular model. This value can also be overridden or set by user input to adjust the model to a correct depth.

Missing images are next identified. Automatic identification is done by looking at several factors, including numbering of the image files, content of the image files and validity of the image files. Image files in a sequence are often numbered sequentially. The sequence of numbers is analyzed, and any missing numbers in the sequence are flagged as missing images. The content of images is analyzed, and images missing sufficient data (e.g. An image which is almost or entirely blank) are flagged as missing images. Invalid image files are files which do not open as a valid image of the type being used. Automatic generation of the three dimensional image treats flagged images as missing. Alternatively, or in conjunction, a user can review and change missing images, as well as flag additional images as missing.

Images are then aligned between frames where required. An image is determined to be out of alignment if the points of the perimeter are out of alignment from both adjacent images. Therefore, if three sequential images have perimeters occupying the same region of the image, adjusted for scale and changes in shape, the images are determined to be aligned. If the image in the center is out of alignment from the adjacent images, the image is adjusted to be in line by comparing features between the images and aligning them. This alignment uses the full image and not just the perimeter.

The final model is created by interpolating missing images. The final number of images required is determined, and the number of images that must be added between each existing image pair. Multiple passes are taken to add the required images. In each pass, one image is added between each existing pair by interpolating the data that exists in the images. Therefore, in a sequence containing 5 images, there will be 9 images after one pass. After a second pass, there will be 16 images. This continues until the desired number of images has been met or exceeded.

The following non-exhaustive methods, systems and system components are disclosed herein:

- A method for providing an augmented or virtual reality surgical overlay, comprised of elements including, but not limited to, heads-up-display (HUD), medical imaging display, vital statistics display, patient information display, procedural information and other data.
- A method for displaying surgical targets and other pertinent medical and/or anatomical data in an augmented or virtual reality surgical environment.
- A method for providing an augmented or virtual reality surgical overlay for laparoscopic procedures, comprised of elements including, but not limited to, mapping of laparoscopic device path, display of laparoscopic device position, display of laparoscopic imaging data, and system for taking notes generally and related to specific points.
- A method for providing an augmented or virtual reality anatomical display, comprised of elements including, but not limited to, anatomical diagramming and labelling, veterinary anatomy, and dissection simulations.
- A method for combining gross anatomy with problem based learning (PBL).
- A method for providing an augmented or virtual reality medical simulation, comprised of elements including, but not limited to, diagnostic simulations, surgical simulations, procedural simulations, previewing surgeries based on patient imaging, and group simulations for purposes such as teaching.
- A method for displaying a heads-up display (HUD) in augmented or virtual reality composed of two or three dimensional images superimposed on or integrated into the environment being viewed.
- A method of using augmented or virtual reality combined with artificial intelligence for the purpose of testing and teaching materials to students.
- A method for augmented or virtual reality simulation for the purpose of training a user in first aid.
- A method for doing intelligence quotient testing using augmented or virtual reality.
- A method for controlling the visualization of a three dimensional object displayed in virtual reality, augmented reality, or other virtual space comprising the steps of determining the requisite change in visualization, and updating the three dimensional object. An apparatus for controlling the visualization of a three dimensional object displayed in virtual reality, augmented reality, or other virtual space comprising a means of determining the requisite change in visualization, and a means for updating the three dimensional object. The process may be performed automatically by a system or may be guided interactively by an operator. Applications include, but are not limited to, virtual reality, augmented reality and three dimensional printing.
- A method for visualizing medical imaging data in augmented reality, virtual reality, or other virtual environment, comprising the steps of locating the subject, determining subject position, determining subject orientation, and rendering the medical imaging data. An apparatus for visualizing medical imaging data in augmented reality, virtual reality, or other virtual environment, comprising a means for locating the subject, a means for determining subject position, a means for determining subject orientation, and a means for rendering the medical imaging data. The process may be performed automatically by a system or may be guided interactively by an operator. Applications include, but are not limited to, visualization for the purpose of surgical procedures, visualization for the purpose of medical testing, visualization for the purpose of surgical training, visualization for the purpose of medical training, visualization for the purpose of physiotherapy, visualization for the purpose of laser surgery, and visualization for the purpose of physical diagnostics.
- A method for enhancing positional location in augmented reality using gadolinium markers.
- A method and apparatus for constructing a three dimensional model comprising the steps of determining image separation distance, identifying missing images, aligning source image and constructing missing image data, and merging the images to form a three dimensional model.
- A method for teaching students using augmented or virtual reality combined with artificial intelligence.

Any of the various methodologies disclosed herein and/or user interfaces for configuring and managing same may be implemented by machine execution of one or more sequences instructions (including related data necessary for proper instruction execution). Such instructions may be recorded on one or more computer-readable media for later retrieval and execution within one or more processors of a special purpose or general purpose computer system or consumer electronic device or appliance, such as the various system components, devices and appliances described above (e.g., programmed processor(s) as shown in FIG. 1). Computer-readable media in which such instructions and data may be embodied include, but are not limited to, non-volatile storage media in various non-transitory forms (e.g., optical, magnetic or semiconductor storage media) and carrier waves that may be used to transfer such instructions and data through wireless, optical, or wired signaling media or any combination thereof. Examples of transfers of such instructions and data by carrier waves include, but are not limited to, transfers (uploads, downloads, e-mail, etc.) over the Internet and/or other computer networks via one or more data transfer protocols (e.g., HTTP, FTP, SMTP, etc.).

In the foregoing description and in the accompanying drawings, specific terminology and drawing symbols have been set forth to provide a thorough understanding of the disclosed embodiments. In some instances, the terminology and symbols may imply specific details that are not required to practice those embodiments. For example, any of the specific dimensions, numbers of components (cameras, projections, sensors, etc.), component circuits or devices and the like can be different from those described above in alternative embodiments. Additionally, links or other interconnection between system components or functional blocks may be shown as buses or as single signal lines. Each of the buses can alternatively be a single signal line, and each of the single signal lines can alternatively be buses. Signals and signalling links, however shown or described, can be single-ended or differential. The term "coupled" is used herein to express a direct connection as well as a connection through one or more intervening circuits or structures. Device "programming" can include, for example and without limitation, loading a control value into a register or other storage circuit within the device or system component in response to a host instruction (and thus controlling an operational aspect of the device and/or establishing a device configuration) or through a one-time programming operation (e.g., blowing fuses within a configuration circuit during device production), and/or connecting one or more selected pins or other contact structures of the device to reference voltage lines (also referred to as strapping) to establish a particular device configuration or operation aspect of the device. The terms "exemplary" and "embodiment" are used to express an example, not a preference or requirement. Also, the terms "may" and "can" are used interchangeably to denote optional (permissible) subject matter. The absence of either term should not be construed as meaning that a given feature or technique is required.

Various modifications and changes can be made to the embodiments presented herein without departing from the broader spirit and scope of the disclosure. For example, features or aspects of any of the embodiments can be applied in combination with any other of the embodiments or in place of counterpart features or aspects thereof. Accordingly, the specification and drawings are to be regarded in an illustrative rather than a restrictive sense.

What is claimed is:

1. A system for identifying abnormalities within an interior of a physical subject, the system comprising:
    a data reception interface configured to receive morphological data captured during an imaging procedure of the interior of the physical subject, the morphological data comprising first morphological data of an entirety of a first three-dimensional physical feature and second morphological data of an entirety of a second three-dimensional physical feature in the interior of the physical subject;
    a user interface configured to receive a user input from a user; and
    at least one processor configured to:
        render a first three-dimensional virtual image of the interior of the physical subject, the first three-dimensional virtual image including the first and second three-dimensional physical features in situ, wherein, in the first three-dimensional virtual image, the second three-dimensional physical feature at least partially obscures from view the first three-dimensional physical feature,
        automatically analyze the morphological data to identify a defect in the first three-dimensional physical feature,
        automatically, without user intervention, select a display depth for a second three-dimensional virtual image,
        identify a subset of the morphological data in accordance with the selected display depth, the subset of the morphological data not including the second morphological data,
        after identifying the defect in the first three-dimensional physical feature, render the second three-dimensional virtual image of the interior of the physical subject, the second three-dimensional virtual image including only the subset of the morphological data, the second three-dimensional virtual image exposing the defect in the first three-dimensional physical feature, and
        in response to the user input, change an orientation of the first three-dimensional physical feature in the second three-dimensional virtual image.

2. The system recited in claim 1, wherein the at least one processor is configured to render the second three-dimensional virtual image of the interior of the physical subject by conducting a negative space exploration.

3. The system recited in claim 1, wherein the at least one processor is configured to render the second three-dimensional virtual image of the interior of the physical subject as an overlay on the physical subject, such that the first three-dimensional physical feature is shown in situ relative to the physical subject.

4. The system recited in claim 3, wherein the at least one processor is further configured to, before rendering the second three-dimensional virtual image of the interior of the physical subject:
    determine an orientation of the physical subject,
    and wherein the at least one processor is configured to render the second three-dimensional virtual image of the interior of the physical subject as an overlay on the physical subject by determining an overlay orientation of the second three-dimensional virtual image.

5. The system recited in claim 1, wherein the morphological data is first morphological data, and wherein the at least one processor is further configured to:
    automatically, without human intervention, detect a change in the defect in the first three-dimensional physical feature with respect to second morphological data, the second morphological data having been captured during a prior imaging procedure of the interior of the physical subject.

6. The system recited in claim 5, wherein the change in the defect comprises one or more of a size or a shape.

7. The system recited in claim 1, wherein the defect is associated with a medical condition.

8. The system recited in claim 1, wherein the user input is a first user input, and wherein the at least one processor is further configured to:
    obtain a second user input identifying the morphological data.

9. A method of identifying abnormalities within an interior of a three-dimensional physical subject, the method comprising:
    receiving morphological data captured during an imaging procedure of the interior of the three-dimensional physical subject, the morphological data comprising first morphological data of an entirety of a first three-dimensional physical feature situated in the interior of the three-dimensional physical subject;
    rendering a first three-dimensional virtual image of the interior of the three-dimensional physical subject;
    automatically analyzing the morphological data to identify a defect in the first three-dimensional physical feature;
    automatically, without user intervention, selecting a display depth for a second three-dimensional virtual image;
    identifying a subset of the morphological data in accordance with the selected display depth, the subset including less than all of the morphological data; and
    after identifying the defect in the first three-dimensional physical feature, rendering the subset of the morphological data to display the second three-dimensional virtual image of the interior of the three-dimensional physical subject, the second three-dimensional virtual image exposing the defect in the first three-dimensional physical feature.

10. The method recited in claim 9, wherein rendering the subset of the morphological data comprises performing a negative space exploration.

11. The method recited in claim 9, wherein rendering the subset of the morphological data comprises rendering the second three-dimensional virtual image of the interior of the three-dimensional physical subject as an overlay on the three-dimensional physical subject, such that the first three-dimensional physical feature is shown in situ relative to the three-dimensional physical subject.

12. The method recited in claim 11, further comprising, before rendering the subset of the morphological data, determining an orientation of the three-dimensional physical subject, and wherein rendering the second three-dimensional virtual image of the interior of the three-dimensional physical subject as an overlay on the three-dimensional physical subject comprises determining an overlay orientation of the second three-dimensional virtual image.

13. The method recited in claim 9, wherein the morphological data is first morphological data, and further comprising:
   automatically, without human intervention, detecting a change in the defect in the first three-dimensional physical feature with respect to second morphological data, the second morphological data having been captured during a prior imaging procedure of the interior of the three-dimensional physical subject.

14. The method recited in claim 13, wherein the change in the defect comprises one or more of a size or a shape.

15. The method recited in claim 9, wherein the defect is associated with a medical condition.

16. The method recited in claim 9, further comprising:
   obtaining a user input identifying the first three-dimensional physical feature.

17. The method recited in claim 9, further comprising:
   obtaining a user input identifying the three-dimensional physical subject.

18. The method recited in claim 9, further comprising:
   obtaining a user input identifying the morphological data.

\* \* \* \* \*